(12) United States Patent
Sirat

(10) Patent No.: US 9,250,185 B2
(45) Date of Patent: Feb. 2, 2016

(54) METHOD AND DEVICE FOR SUPERRESOLUTION OPTICAL MEASUREMENT USING SINGULAR OPTICS

(75) Inventor: Gabriel Y. Sirat, Paris (FR)

(73) Assignee: Bioaxial SAS (FR)

( * ) Notice: Subject to any disclaimer, the term of this patent is extended or adjusted under 35 U.S.C. 154(b) by 199 days.

(21) Appl. No.: 13/822,355

(22) PCT Filed: Oct. 14, 2011

(86) PCT No.: PCT/FR2011/000555
§ 371 (c)(1),
(2), (4) Date: Mar. 12, 2013

(87) PCT Pub. No.: WO2012/049381
PCT Pub. Date: Apr. 19, 2012

(65) Prior Publication Data
US 2013/0176574 A1  Jul. 11, 2013

(30) Foreign Application Priority Data
Oct. 15, 2010  (FR) ..................................... 10 04067

(51) Int. Cl.
*G01B 11/02* (2006.01)
*G01N 21/64* (2006.01)
(Continued)

(52) U.S. Cl.
CPC ............ *G01N 21/64* (2013.01); *G01N 21/6428* (2013.01); *G01N 21/6458* (2013.01); *G02B 21/0056* (2013.01); *G02B 21/0072* (2013.01); *G02B 21/0076* (2013.01); *G01B 11/25* (2013.01)

(58) Field of Classification Search
CPC .......... G01N 21/6458; G01N 21/6428; G01N 21/64; G01B 11/25; G06T 7/004; G06T 7/0042; G02B 21/0056; G02B 21/0072; G02B 21/0076
See application file for complete search history.

(56) References Cited

U.S. PATENT DOCUMENTS 7,324,273 B2    1/2008  Gweon et al. ................. 359/386
7,541,600 B2    6/2009  Neuhauser et al. ........ 250/491.1
(Continued)

FOREIGN PATENT DOCUMENTS

WO    WO 2009/066253 A2    5/2009    ............... G02B 3/00

OTHER PUBLICATIONS

Stefan Hell, "Far Field Optical Nanoscopy", Science 316, 1153 (2007).*
(Continued)

*Primary Examiner* — Michael A Lyons
(74) *Attorney, Agent, or Firm* — Sunstein Kann Murphy & Timbers LLP

(57) ABSTRACT

The invention proposes an optical method of measurement and an optical apparatus for determining the spatial position of at least one luminous nanoemitter of a sample, the method comprising: the projection of a sequence of at least two compact luminous distributions of different topological families onto the sample, the detection of the light reemitted by said at least one luminous nanoemitter of the sample; the generation of at least one optical image for each luminous distribution, on the basis of the light detected; and the algorithmic analysis of the optical images to obtain information regarding the location of said at least one luminous nanoemitter. The invention further relates to an optical method of measurement and an optical apparatus for determining the spatial position of a plurality of point light sources, the method comprising the detection of the light emitted by the plurality of point light sources; and the separation of the light emitted on a plurality of detectors for simultaneous or sequential detections; the proportion of the light emitted by a point light source, channeled to a specific detector, being dependent on the spatial position of said point light source; and the generation of the optical images on the basis of the light detected; and the algorithmic analysis of the optical images to obtain an item of information regarding the location of the plurality of point light sources.

26 Claims, 13 Drawing Sheets

(51) Int. Cl.
*G02B 21/00* (2006.01)
*G01B 11/25* (2006.01)

(56) References Cited

U.S. PATENT DOCUMENTS

| | | | | |
|---|---|---|---|---|
| 8,084,754 | B2* | 12/2011 | Hell | G01N 21/6428 250/459.1 |
| 8,514,685 | B2 | 8/2013 | Sirat | 369/112.01 |
| 8,542,712 | B2 | 9/2013 | Rafailov et al. | 372/66 |
| 2002/0141052 | A1 | 10/2002 | Iketaki | 359/386 |
| 2003/0137645 | A1* | 7/2003 | Fluckiger | 356/4.01 |
| 2003/0210405 | A1 | 11/2003 | Feldman | 356/511 |
| 2004/0212799 | A1* | 10/2004 | Hell | G01N 21/6428 356/317 |
| 2007/0070496 | A1 | 3/2007 | Gweon et al. | 359/386 |
| 2008/0068588 | A1* | 3/2008 | Hess et al. | 356/36 |
| 2009/0168613 | A1* | 7/2009 | Sirat | 369/18 |
| 2009/0242798 | A1* | 10/2009 | Bewersdorf et al. | 250/458.1 |
| 2012/0104279 | A1 | 5/2012 | Reuss et al. | 250/458.1 |
| 2014/0145093 | A1* | 5/2014 | Hendriks | G01N 21/6458 250/459.1 |

OTHER PUBLICATIONS

Tina Zuchner, Antonia Failla, and Alfred Meixner, "Light Microscopy with Donut Modes: A Concept to Detect, Characterize, and Manipulate Individual Nanoobjects" Chem. Int. Ed. 2011, 50, 5274-5293.*

Jan Keller, Andreas Schonle, and Sefan W. Hell, "Efficient fluorescence inhibition patterns for RESOLFT microscopy" Optics Express vol. 15, No. 6 Published Mar. 19, 2007.*

Ram Oron, Shmuel Blit, Nir Davidson, Asher A. Friesem, Zeev Bomzon, and Erez Hasman, "The formation of laser beams with pure azimuthal or radial polarization", Appiled Physics Letters 77 3322 Published Nov. 20, 2000.*

Berry et al., "Conical diffraction: observations and theory," *Proc. R. Soc. A*, vol. 462, pp. 1629-1642 (Feb. 2006).

Abdolvand et al., "Conical refraction Nd:KGd($WO_4$)$_2$ laser," *Opt. Express*, vol. 18, No. 3, pp. 2753-2759 (Feb. 2010).

Berry, "Conical diffraction from an N-crystal cascade," *J. Opt.*, vol. 12, No. 8, 9 pages (2010).

Boruah, "Lateral resolution enhancement in confocal microscopy by vectorial aperture engineering," *Appl. Optics*, vol. 49, No. 4, pp. 701-707 (Feb. 2010).

Haeberlé et al., "Saturated structured confocal microscopy with theoretically unlimited resolution," *Opt. Comm.*, vol. 282, pp. 3657-3664 (2009).

Lunney et al., "The ins and outs of conical refraction," *Europhysics News*, vol. 37, No. 3, pp. 26-29 (2006).

Peet, "Biaxial crystal as a versatile mode converter," *J. Opt.*, vol. 12, pp. 1-4 (2010).

Vlokh et al. "Appearance of Optical Vortex at Conical Refraction. Examples of $NaNO_2$ and $YFeO_3$ Crystals," *Ukr. J. Phys. Opt.*, vol. 4, No. 2, p. 90-93 (Jan. 2003).

* cited by examiner

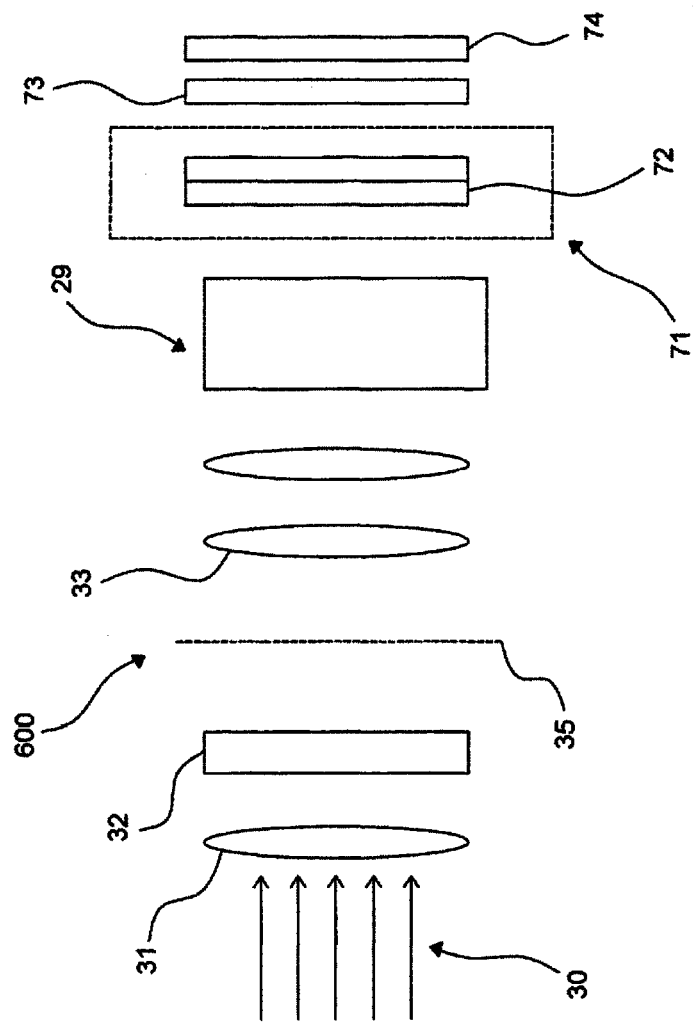

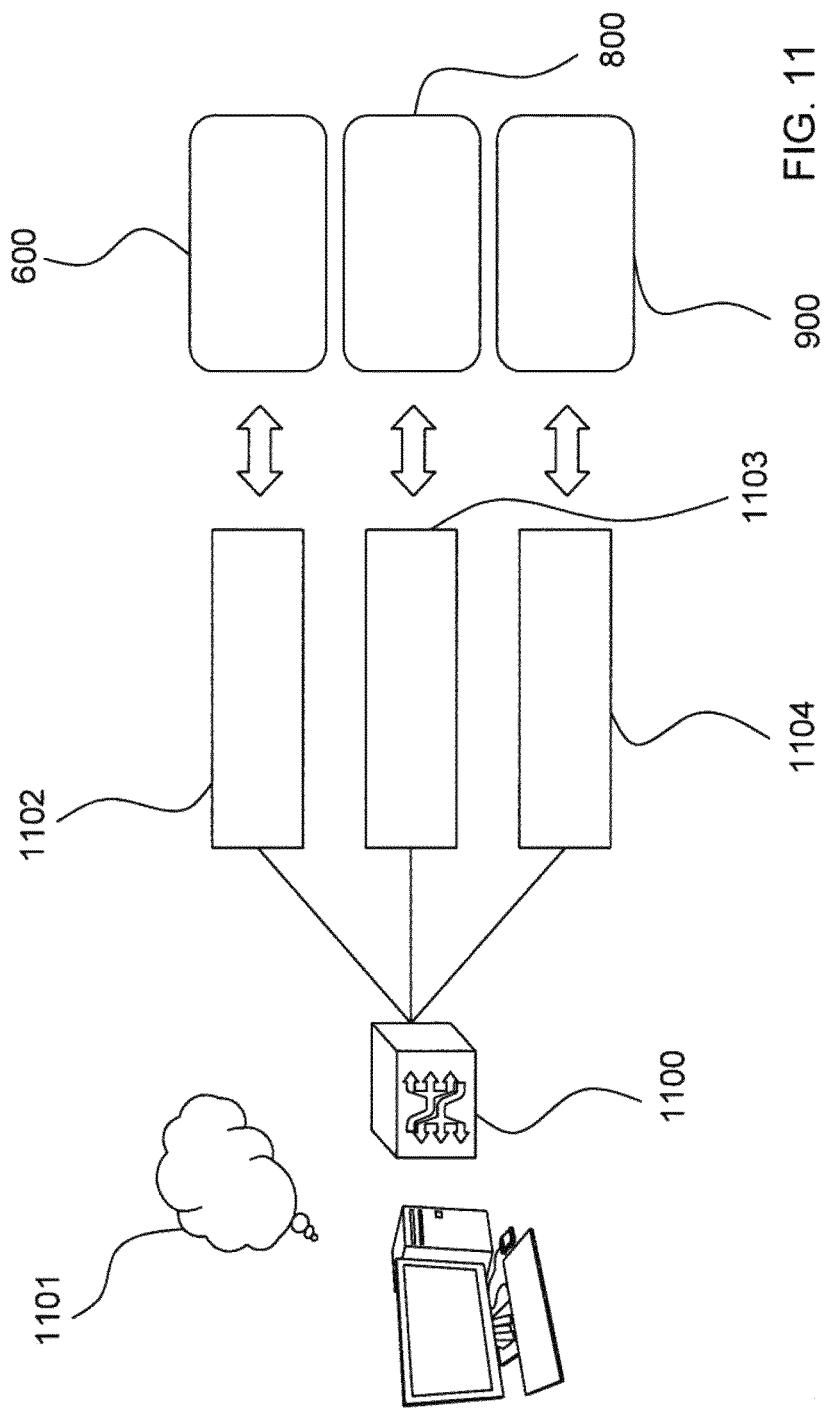

METHOD AND DEVICE FOR SUPERRESOLUTION OPTICAL MEASUREMENT USING SINGULAR OPTICS

CROSS-REFERENCE TO RELATED APPLICATIONS

This application is a national phase entry of PCT/FR2011/000555, file Oct. 14, 2011, which claims the benefit of French application no. FR1004067, filed Oct. 15, 2010, the entire contents of which are incorporated by reference herein.

BACKGROUND

The present invention relates to a method and an optical measuring device. It finds applications in particular in microscopy, for example in the field of biology and the acquisition of biological information from optical observation.

A microscope is an optical instrument generally used to view, analyze or measure objects too small for the naked eye.

We use the term biological to describe any biological entity in life sciences, regardless of its origin, human, animal or vegetal and of the purpose of the observation, be it for research, diagnostic or therapeutic application. This term includes the medical uses of the method described. Microscopy is used in the field of biology, for example, to observe, study and measure biological entities (objects) and their dynamics.

The usual definitions are used for: optical diffraction limit, Rayleigh criterion, Airy disk and its radius and diameter. We use in the context of the invention, the terms of superresolution, superresolved, superresolution imaging and superresolution microscopy to describe optical data acquisition, optical imaging and microscopy at a resolution higher than the optical diffraction limit. The usual definitions are used for fluorescence and for fluorophores.

Referring now to FIG. 1, which shows an illustration of the paradigm of Microscopy, 100, in the field of Biology.

Microscopy comprises the illumination, by a light source, not shown, using a microscope, 10, of a biological sample, 11, and the time-dependent measurement, using either visual observation or a detection module 12, of the light emitted by the sample.

The sample in Biology comprises a single—or a plurality—of different biological entities, 13 and 14, positioned at different positions.

Examples of such objects are, among others, a cell, a virus, a protein and a DNA fragment.

Fluorescence microscopy is one of the variants of microscopy, it has replaced in many biological applications, the other microscopy techniques.

A fluorescence microscope is an optical microscope used to study properties of organic or inorganic substances using the phenomena of fluorescence instead of, or in addition to other modalities such as reflection and absorption.

We refer again to FIG. 1, describing a fluorescence microscope; in fluorescence microscopy fluorophores, tiny point sources, 15 to 18, based on the physical phenomenon of one photon fluorescence, are fixed at specific positions of predetermined biological objects, 13 and 14; the light emitted by the fluorophores is observed instead of observing the light emitted by the biological objects, 13 and 14, themselves.

The sample is illuminated by light of wavelength, or specific wavelengths, which is absorbed by the fluorophore, thereby inducing the emission of light at different, higher, wavelengths.

The illumination light is separated from the emitted fluorescence, which is lower, by the use of a spectral emission filter.

Fluorophores have become an important tool for the visualization of biological objects. The activity and the biological information including details above the limit of resolution of 200 nm are systematically viewed and measured using fluorescence microscopy. This resolution limit is derived from the Rayleigh criterion, which in the best case, reaches 200 nm in systems designed specifically. For a long time, until the emergence of superresolution techniques described below, it was assumed that optical techniques, including fluorescence microscopy, are unable to visualize details smaller than the Rayleigh criterion, which is about 200 nm.

However, other fundamental biological activities also occur at scales smaller than 200 nm in biological samples. At this level of spatial resolution, important phenomena can be observed: the biological processes at the scale of intracellular, cell information transfer, the folding and unfolding of the proteins and changes in the DNA and RNA. For example, the measurement of this intracellular information open new avenues for understanding the biological activity, and lead to progress in understanding and monitoring of research and medical diagnostics.

The main implementations of fluorescence microscopy, as described in detail in the literature, are the confocal microscope, often used in a scanning configuration or spinning disc microscope, and the wide-field imaging microscope.

Referring now to FIG. 2 which is a simplified representation of a confocal fluorescence microscope of the prior art 200.

A confocal fluorescence microscope, FIG. 2 is an optical instrument. Its main hardware components are shown in FIG. 2. They include:
  a light source, 20,
  an optomechanical frame not shown
  a cube filter, 21,
  a microscope objective 22, and,
  a detector assembly, 23,
  a processing unit, not shown.

The light source 20, which may be an arc lamp or a laser, creates light energy necessary for fluorescence.

The Optomechanical frame, not shown, is the support of all the optical components and auxiliary optics and includes alignment capacities.

It also includes optical elements, not shown, capable of shaping the beam to allow its focus point of a minimum size by means of the microscope objective.

It can also comprise, in a confocal scanning fluorescence, a spatial or angular scanning mechanism, not shown, to change the position of the point source with respect to the object to be measured.

The scanning mechanism can alternatively
  mechanically translate the object, for example by using a translation plate,
  optically scan the beam on the object, for example using a set of galvanometric mirrors or acousto-optical translators, or
  use any combination of these translation means, mechanical or optical.

In a confocal scanning fluorescence, the information is collected point by point, using the scanning mechanism.

It can also comprise, in a rotating disk type confocal fluorescence, a rotating disc having a plurality of pinholes, allowing the simultaneous projection of a plurality of points. In a confocal fluorescence rotating disk, a set of points, corresponding to the pinhole is acquired at any time and the rotation of the disk allows to scan the entire surface of the sample for a given longitudinal position.

The cube of filters, 21, channels the different optical signals and avoids contamination of the fluorescence signal by the emission. The cube is composed of filters: excitation filter, 210 dichroic mirror, 2 11, and emission filter 212. The filters and the dichroic mirror are selected according to the wavelength of excitation and emission spectral characteristics of the fluorophore.

The microscope objective 22 focuses the light created by the source in the focal plane of the lens 24, a light distribution pattern of small size, the optimum light distribution consisting of the Airy disk. The microscope objective 22, also collects back fluorescent light emitted by the fluorophores.

For a confocal scanning fluorescence the system can be descanned, that is to say, the return light can pass through the scanning mechanism to compensate for the translation due to scanning.

A detector lens, 25, creates, in the image plane of the detector 26, a magnified image of the focal plane of the lens 24.

A confocal hole, 27, is theoretically placed in the image plane of the detector 26. In most practical systems, the confocal hole, 27, is placed in an intermediate imaging plane, not shown, and reimaged onto the image plane of the detector 26.

The assembly of the detector, 23, detects the fluorescent intensity in the overall illuminated volume, and converts it into digital signal. For a confocal scanning microscope, the detector assembly comprises a detector of a single element, such as a PMT or SPAD. For a confocal microscope using a rotary disc, the detector assembly is comprised of a matrix of detector elements, such as a CCD, a EMCCD, a CMOS or a matrix of SPAD.

All components mounted from the light source to the dichroic filter is the illumination path, 201. The detection channel, 202, represents all the components mounted from the dichroic filter to the assembly of the detector.

The elementary optical process of a confocal microscope can be segmented into six steps:
  Projecting light on the volume analyzed
  Fluorescent light emission by fluorophores
  Imaging of the fluorophores in the focal plane
  Limitation in the focal plane of light analyzed by confocal hole
  Integration of light analyzed by a photoelectric detector
  Display of the measured intensity as a pixel value in an image Fluorescence microscopes are available from several manufacturers, such as Nikon, Zeiss, Leica and Olympus. Fluorescence microscopes can be either standard microscopes suitable for fluorescence or microscopes optimized specifically for fluorescence. Modern microscopes are versatile instruments capable of operating in many different modalities, including, but not limited to, fluorescence modalities, using the same platform and most optomechanical components. Most fluorescence microscopes are developed as an open platform, capable of performing several additional features with minimal modifications. Other fluorescence microscopes are instruments dedicated, adapted for a specific task, such as medical diagnosis or pharmaceuticals.

New optical methods, methods for superresolution are capable of discriminating fluorophores, below the Rayleigh criterion. These methods are being developed by several companies, laboratories and researchers and some of the instruments using these methods, the superresolution microscopes, are commercially available. Several comparative analysis of superresolution methods have recently been published in the literature, such as the article written by Ricardo Henriques and Mr. Musa Mhlanga ("PALM and STORM: What hides beyond the Rayleigh limit?", *Biotechnology Journal*, 4, 846-857 (2009)), or the article written by Kelly Rae Chi ("Super resolution microscopy: breaking the limits", *Nature Methods*, 6, 15-18 (2008)).

An updated bibliography on the superresolution is on the website of the company Zeiss Co. ("Zeiss Microscopy and image analysis", (2011), retrieved at http://www.zeiss.com/4125681C00466C26/?Open) and on the website of the company Nikon Co. ("MicroscopyU: the source for Microscopy Education" (2011) retrieved at http://www.microscopyu.com/).

Different existing methods of microscopy and existing microscopes, not incorporating the superresolution, allow microscopic observation up to the optical diffraction limit. This reduces their field of use to a limited set of applications.

New superresolution techniques allow to obtain information beyond the resolution limit. The main problem of all existing superresolution techniques is that the envelope of performance, expressed in terms of lateral resolution of longitudinal resolution, speed, light intensity necessary for phototoxicity in the biological object, of ability to measure different objects, is very limited.

In addition, most of the methods and instruments can provide superresolution either a good lateral resolution or a good longitudinal resolution, but rarely both.

In addition, all these instruments are complex and require a highly skilled operator.

In addition, these instruments can generally observe a small part of biological specimens due to strong operational limitations, such as, for some of them, a shallow depth of field or a requirement of very high light intensities, harmful to cells.

Another problem with the methods and instruments of super resolution, is that most of them are able to recover in the illuminated volume, the attributes of a single fluorophore, but fail to recognize the presence of simultaneously several fluorophores and measuring their attributes.

An additional problem with the methods and instruments of superresolution is that these methods and instruments are presented to users and perceived by them as a general tool, able to replace the standard or confocal microscopes. However, the methods and instruments superresolution lack the simplicity, robustness, ease of use and competitive prices of standard microscopes which hinders their use as research tools or as general diagnostic tools.

Another problem with existing superresolution methods and tools is that most of these methods and tools are designed as stand-alone instruments designed to replace standard microscopes. Such an approach requires the replacement of existing instruments and the renewal of all systems and devices all the knowledge and know-how related to microscopy platforms and developed over many years.

Another problem with most methods and instruments fluorescence microscopy and superresolution is that these methods and tools are designed on a paradigm of image acquisition, the entity for which basic information is—or more images, or—or more—ROI regions—Region Of Interest bi- or three-dimensional. Algorithmic, systemic and superresolution methods described later in the context of the invention will, by their inherent flexibility, the development of new strategies of acquisition. These acquisition procedures, dynamic and selective, will be defined by an optimized sequence acquisition and interactive and deferred processing. They allow a more sophisticated optimization of the useful information, as defined by criteria based on the shape, geometry and dynamics of one or more fluorescent objects, separately or relative one to the other.

So there is still an urgent need to provide superresolution methods and tools and algorithms methods capable of measuring with high accuracy the attributes of a fluorophore. It is also necessary to provide methods and tools to detect and quantify the presence of multiple fluorophores placed in the same volume illuminated.

SUMMARY

A goal of at least one embodiment of the present invention is to provide a technique for superresolution fluorescence microscopy in Biology and more generally to life sciences, and additionally to pharmacology, medicine and diagnostics, that will overcome the shortcomings of the prior art devices.

One of the goals of at least one embodiment of the present invention is to provide a technique for superresolution fluorescence microscopy in biology to achieve an optical system that is capable of measuring with high accuracy the attributes of a fluorophore and recognizing and measuring the attributes of multiple fluorophores located in the same illuminated volume.

Another goal of at least one embodiment of the invention is to provide a technique for superresolution fluorescence microscopy in biology to measure with high precision the attributes of a fluorophore.

Another goal of at least one embodiment of the invention is to provide a technique for superresolution fluorescence microscopy in biology that acquires and measure with great precision, the attributes of multiple fluorophores present in the same illuminated volume.

To this end, a first aspect of the invention provides a method of optical measurement to determine the spatial position of at least one light nanoemitter on a sample, the method comprising:
- projecting a sequence of at least two light distributions of different topological families on the sample,
- detecting of the light reemitted by said at least one light nanoemitter from the sample; generating at least one optical image for each light distribution, from the detected light, and
- analyzing algorithmically the optical images to obtain a location information of said at least one light nanoemitter.

The detection may comprise the detection of the reflected light at a mean wavelength $\lambda$. The reflected light can be collected by a high numerical aperture objective. Both distributions can be compact.

The plurality of distributions may be generated sequentially in time, or created simultaneously.

According to an embodiment the two compact light distributions are collocated on the sample.

According to one embodiment said at least two compact light distributions of different topological families are created by interference between a regular wave and a singular wave, or between two singular waves, and spatial differentiation between said at least two distributions is created by varying at least one of the following parameters:
- a) at least one of the parameters of the regular wave;
- b) at least one parameter of at least one singular wave and
- c) a phase difference between the regular wave and the singular wave or between two singular waves.

The various parameters may include amplitude, phase, polarization, coherence, for example.

According to one embodiment of the process included the creation from an incident light wave, two light collocated waves one regular and one singular.

According to one embodiment the method further includes the separation of an incident regular wave, into two regular waves following separate geometric paths; transforming, at least one of the regular optical waves in a singular optical wave and fusion of the two created emerging optical waves.

According to one embodiment the method further includes at least one of the following steps:
- control of the relative amplitude of the regular—and/or singular waves;
- control, following a predetermined sequence, of the polarization and/or the phase state of the input or output light wave from a crystalline sub-module creating regular and singular waves; the control of the shape of singular or regular waves, and
- aligning the central position of the light distribution of a wave in relation to the other.

According to one embodiment, the process further included formatting, statically or dynamically, the emerging polarization of the said superimposed light distributions, able to mitigate vector effects, on the shape and size of said compact light distributions, effects created by a high numerical aperture lens used for generating optical images, by shaping the emerging polarization by providing a static, rotationally symmetrical, polarization state such that a circular polarization, radial or azimuthal and/or a dynamic polarization state.

According to one embodiment said at least two light distributions are created by controlling the intensity of the different modes of a multimode laser.

According to one embodiment, a region of a size substantially less than a mean wavelength $\lambda$ of the reflected light exists in the sample, wherein the value of a specific mathematical combination of the intensities of said at least compact two light distributions of different topological families is positive for lateral positions of said light distribution portion included in said region, and wherein said specific combination mathematical approaches zero in all other parts of the light distribution beyond said region.

According to one embodiment at least one nanoemitter is a fluorophore with a sequence of fluorescence light intensities which depends of the incident intensity of the sequence of compact light distributions of different topological families on said fluorophore thus characterizing the spatial position of said fluorophore.

According to another embodiment at least two of the nanoemitters are fluorophores, located at different spatial positions, each fluorophore emitting light with an intensity depending on the incident intensity of the sequence of compact light distributions of different topological families on the said at least two fluorophores thereby characterizing the spatial position of at least two fluorophores.

According to one embodiment a region whose size is substantially smaller than the wavelength $\lambda$ of the reflected light, exists on the sample, wherein a comparison of a plurality of mathematical combinations of the said sequence of compact light distributions of different topological families, can differentiate between at least one of the following:
- a) a single light nanoemitter;
- b) a plurality of collocated light nano emitters, and
- c) a plurality of light nanoemitters located at a distance from each other, thereby determining the distance between the light nano emitters.

According to one embodiment the method further comprises varying the sequence of said at least two light distributions and/or the position of the sequence of said at least two light distributions as a function of measured data or external information.

According to one embodiment, the projection of light distributions of different topologies is created by the conical diffraction and modified by a variation of the polarization states of input and output of at least one crystal creating the conical diffraction effect.

According to one embodiment, the spatial position of at least one measured light nanoemitter is the lateral position of said at least one light nanoemitter.

A second aspect of the invention provides a method of optical measurement to determine the spatial position of a plurality of light point-sources the method comprising detecting light emitted by the plurality of light point-sources; and the separation of the light emitted on a plurality of sensors for simultaneous or sequential detection; and the proportion of the light emitted by a light point-source, channeled to a specific detector, being dependent on the spatial position of said light point-source; and the generation of the optical images from the detected light; and the algorithmic analysis of optical images to obtain a location information of the plurality of light point-sources.

According to one embodiment, each light point-source corresponds to one or more of the several nanoemitters and the method includes a preliminary step comprising the illumination by incident light of the nanoemitters of the sample for detecting the light remitted by nanoemitters for locating the nanoemitters.

According to an embodiment the spatial position measured is the longitudinal position of each light point-source or light nanoemitter.

According to one embodiment, the emitted light is separated according to the longitudinal position of each light point-source or nanoemitter or according to the wavelength emitted by each light point-source or nanoemitter.

According to an embodiment the separation of the emitted light is performed so as to separate, to a plurality of detection channels, the collimated emitted light, emerging from the light sources positioned at the focal plane of the lens, from the non-collimated emitted light emerging from point-sources lying above or beyond the focal plane.

According to one embodiment the method further comprises the parameter variation of the detection channels based on measured data or external information.

According to one embodiment the method further comprises at least one of the following steps:
  generating, from each light point-source, a beam of quasi parallel light, the light beam differing from the parallel light by an angle of convergence or divergence, the value of the angle being a function of the longitudinal position of each light point-source;
  generating, from an incident light wave, two collocated light waves, of orthogonal polarizations and different geometries, one regular and one singular, the ratio of energy between the regular and singular waves being a function of the angle of convergence or divergence of the light beam and through it of the longitudinal position of the point source, the change of polarization or geometry suitable for separating waves regular and singular based on a polarization state thereof, or a geometric shape thereof.

According to one embodiment the method further comprises the separation of the light intensities of the plurality of re-emitted light sources into a plurality of independent channels with orthogonal polarizations, by using a polarization beam splitter, and merging the light intensities emerging from each channel, so that the length of the longitudinal position of the polarization or the pipe geometry of the light intensity in the light is maintained by the merger.

According to one embodiment the method further comprises focusing the light point sources positioned at a given longitudinal position, and the defocusing of the light sources positioned before and after said longitudinal position, the light distribution different from the focus in dependence on the longitudinal position of each point source.

According to one embodiment the method further comprises generating, from the incident light wave, two light waves of different polarizations, the ratio of energy between the waves of different polarizations being a function of the spatial distribution at the point of focusing and through it of the longitudinal position of the light point-source, and the separation of the regular and singular waves on the basis of its state of polarization or of its geometric shape.

According to one embodiment the detection of the light emitted or re-emitted is limited in the focal plane of the microscope objective. according to one embodiment, said at least optical image is generated by using the optical microscope, as for example a confocal microscope A third aspect of the invention provides an optical measuring device for determining the spatial position of at least one light nanoemitter positioned on a sample, the device comprising:
  projection means adapted to project a sequence of at least two compact light distribution different topological families on the sample;
  detecting means adapted to detect the reflected light by said at least one nanoemitter light of the sample,
  generating means adapted to generate at least one image for each optical light distribution, from the detected light, and
  analysis means capable of performing a computational analysis of the optical images to obtain a location information of said at least one light nanoemitter.

According to an embodiment of the means of projections are configured to colocate both compact light distributions on the sample.

According to one embodiment, the projecting means is adapted to create said at least two light distributions by interference between a regular wave and a singular wave or between two singular waves, and to create a spatial differentiation between said at least two distributions by varying at least one of the following parameters:
  a) at least one of the parameters of the regular wave;
  b) at least one parameter of at least one singular wave and
  c) a phase difference between the regular wave and the singular wave or between two singular waves.

According to one embodiment, the device comprises a crystalline sub-module to create from an incident light wave, two collocated light waves one regular and one singular said sub-module lens comprising a thin biaxial crystal and/or a uniaxial crystal.

According to one embodiment the device comprises an optical sub-module adapted to separate a regular incident wave, in two regular waves along separate geometric paths, the sub module being configured to transform at least one of the regular optical waves in an singular optical wave, using processing means comprising at least: a subwavelength grating, the grating step being smaller than the mean wavelength of the reflected light, and a thin biaxial or uniaxial crystal, and wherein the optical module is designed as to combine the two created emerging optical waves.

According to one embodiment the device comprises a polarizer part adapted to control the relative amplitude of regular and singular waves and optionally translating the central position of the light distribution of a wave in relation to the other.

According to one embodiment the device comprises an optical control sub-module of amplitude polarization or phase, comprising at least one controllable or adjustable optical element capable of controlling, in a predetermined sequence, the state of polarization and/or phase of the light input or output wave of the sub-module lens.

According to one embodiment the device comprises a control sub-module, consisting of at least one adjustable optical element capable of controlling the shape of regular or singular waves.

According to one embodiment, the device comprises a polarization analyzer and/or a, static or dynamic, sub-module shaping the emerging polarization of said light distributions, able to mitigate the vector effects on the shape and size of each compact light distribution, effects created by a high numerical aperture of the lens used for generating optical images, shaping the emerging polarization by providing a static polarization state, rotationally symmetrical, such that the circular, radial or azimuthal polarizations and/or a dynamic state of polarization.

In another embodiment, the device comprises a multimode laser, in which the intensity of the laser modes are controllable and at least two compact light distributions of different topological families are created by controlling the intensity of the different modes of laser.

According to one embodiment, a region of a size substantially smaller than the mean wavelength λ of the reflected light exists in the sample, wherein the value of a specific mathematical combination of the intensities of at least two compact light distributions of different topological families created by the illumination means is positive for lateral positions included in said region, and wherein said specific combination mathematical approaches zero in all other parts of the light distribution beyond said region.

According to one embodiment at least one is a nanoemitter is a fluorophore with a sequence of fluorescence light intensities which depends on the sequence of incident compact light distributions of different topological families on said fluorophore thus characterizing the spatial position of said fluorophore.

According to one embodiment at least two of the nanoemitters are fluorophores, located at different spatial positions, each one of the fluorophore with a sequence of light fluorescence intensities which depends on the sequence of incident compact light distributions of different topological families on the at least two fluorophores thereby characterizing the spatial position of the at least two fluorophores.

According to one embodiment a region whose size is substantially smaller than the wavelength λ of the emitted light, exists in the sample, and further comprising a comparator for comparing a plurality of mathematical combinations of said sequence of compact light distributions of different topological families, for differentiating between at least one of the following:
 a) a single light nanoemitter,
 b) a plurality of collocated light nanoemitters, and
 c) a plurality of nano-tagging light-located at a distance from each other, thereby determining the distance between the nano-tagging light.

According to one embodiment, the projecting means is configured to vary the sequence of said at least two light distribution and/or the position of the sequence of said at least two light distributions as a function of measured data or external information.

According to one embodiment, the projecting means comprises at least one conical crystal to perform conical diffraction, and means for varying the polarization states of input and output of said at least one conical crystal.

According to an embodiment configured to measure the lateral position of said at least one light nanoemitter.

According to a fourth aspect, the invention provides an optical measuring device for determining the spatial position of a plurality of light point-sources, the device comprising:
 detecting means adapted to detect the light emitted by the plurality of light point-sources, and
 separation means adapted to separate the reflected light on a plurality of sensors for simultaneous or sequential detection and the proportion of the reemitted light by a light nanoemitter, channeled to a specific detector, being dependent on the spatial position of said light nanoemitter, and
 means for generating image suitable for generating optical images from the detected light, and
 analysis means capable of performing a computational analysis of the optical images to obtain a location information of the plurality of light point-sources of light.

According to one embodiment the device is configured to measure the longitudinal position of each light point-source.

According to one embodiment a point-source comprises one or more nanoemitters of the sample and the device comprises illumination means adapted to illuminate the nanoemitters of the sample by incident light, and detecting means adapted to detect the light remitted by nanoemitters for locating the nano emitters.

For example, a fluorophore can be a nanoemitter.

In one embodiment the separating means are configured to separate the reflected light as a function of the longitudinal position of each light point-source or as a function of the wavelength emitted by each light point-source.

In one embodiment the separating means are configured for separating into a plurality of detection channels, the reflected light collimated emerging from the light point-sources, positioned at the focal plane of the lens, from the remitted non-collimated light emerging from the light point-sources located before or beyond the focal plane.

According to one embodiment the device further comprises variation means to vary the parameters of the detection channels based on measured data or on external information.

According to one embodiment the device further comprises channeling means able to channel the light intensities from the plurality of point sources of light emitted, placed in a small light volume on separate detectors, and/or at separate geometric positions on the same detector, depending on the longitudinal position of each point source.

According to one embodiment the device further comprises a sub-module that interfaces to a microscope objective and to a sub-detection unit and one to the other by auxiliary optics.

According to one embodiment the device comprises optical means adapted to create, from each point source of the light emitted, a beam of quasi parallel light, the light beam differing from the parallel light by an angle of convergence or divergence, and the value of the angle being a function of the longitudinal position of each light point-source.

According to one embodiment the device comprises a crystalline sub-module, or a cascade of crystalline sub-modules, each sub-crystalline module consisting of a biaxial crystal and/or a uniaxial crystal, and auxiliary optics, the aforesaid sub-crystalline module being adapted to create from the incident collocated light wave two light waves of orthogonal polarizations and different geometries, one regular and one singular, the ratio of energy between the regular and singular waves being function of the angle of convergence or divergence of the beam and through him the longitudinal position of the point source emitter.

According to one embodiment the device comprises means for changing the polarization or geometry suitable for separating the regular and singular waves based on a polarization state thereof, or a geometric shape thereof.

According to one embodiment, the device includes
a beam splitter for separating the polarization of light intensities of a plurality of point sources of the emitted light, being part of a longitudinal module of superresolution allowing [lisibility correction] to separate into two independent channels with orthogonal polarizations, and
means for merging the intensities emerging from each channel of the longitudinal module of superresolution, so that the dependence of the longitudinal position of the light intensity of the polarization or the geometry channels is maintained by the merger.

According to one embodiment the device comprises optical means able to focus light point sources of remitted light, positioned at a given longitudinal position, and, to slightly defocus the light sources of the reemitted light, positioned before and after said longitudinal position, the light distribution differing from the focusing in dependence of the longitudinal position of each point source.

According to one embodiment the device comprises means for spatially varying polarization and having at least a uniaxial crystal of variable thickness, a subwavelength grating with step below the mean wavelength of the reflected light and/or a phase waveplate, creating from the incident light wave two light waves of different polarizations, the ratio between the energy of the waves of different polarizations being a function of the spatial distribution at the focusing point and through it of the longitudinal position of the point source emitter.

According to one embodiment, the device comprises polarization or geometry means capable of separating the regular and singular waves on the basis of their polarization states or on their geometric shapes.

In a fifth aspect, the invention provides an optical measurement to determine the spatial position of at least one light nanoemitter on a sample comprising a microscope, for example, a confocal microscope, a measuring device according to one embodiment of the third aspect of the invention, and/or a measuring device according to one embodiment of the fourth aspect of the invention.

According to a sixth aspect, the invention provides a method of optical measurement to determine the spatial position of at least one light nanoemitter on a sample comprising a measuring method according to an embodiment of the first aspect of the invention to determine the lateral position of at least one nanoemitter in a sample, and a measuring method according to an embodiment of the second aspect of the invention for determining the position of at least one longitudinal nanoemitter on a sample.

In another aspect, the invention provides a method of optical measurement consisting of a sequential projection of at least two compact light distributions of topological families on a sample.

In another aspect, the invention provides an apparatus for performing optical measurements with a projector for sequential projecting at least two compact light distributions of different topological families on a sample.

In another aspect, the invention provides an optical system configured to create in sequence, on a sample, at least two light distributions spatially separated from each other, each of said distributions having a diameter less than 1, 5 time the mean wavelength of the reemitted light from the sample, such as combinations of intensities of said distributions creating localized characteristics of a size less than 0.5 said mean wavelength.

In another aspect, the invention provides an optical system including an optical apparatus and a illuminated measurement region, the optical apparatus being configured to sequentially create at least two light distribution spatially separated from each other, and defining a set of points in the measurement region comprising all the points of zero intensity one or another of the distributions, a point located in the region close to a measurement point of said assembly being less than or equal to 0, 5 of the radius of the measuring region.

In another aspect, the invention provides an optical system comprising an optical device and a measurement region to be illuminated, the optical device being configured to sequentially create at least two light distributions spatially differentiated from each other and defining a set of points in the illuminated measurement region, comprising all points of zero intensity and local intensity maximum in one or other of the distributions, a point located near a point of said assembly being less than or equal to ⅙ of the diameter of the measuring region.

In another aspect, the invention provides an optical apparatus, and a compact measuring region having a line passing through the center of the measurement region, the optical apparatus being configured to create a light distribution spatially differentiated, the ratio energy between the intensity along the line passing through a maximum, a minimum and another maximum.

In another aspect, the invention provides a lateral superresolution module comprising an optical device adapted to sequentially create at least two light spots spatially differentiated with a diameter less than 1 5 times the emitted average wavelength $\lambda$, such as combinations of the intensities of said spots create localized details of a size less than 40% of the wavelength $\lambda$ An object of at least one embodiment is to provide a new device, a module for lateral superresolution, comprising an optical device adapted to create at least two light spots spatially differentiated from a diameter less than 1, 5 times the wavelength, $\lambda$, such as localized features of combinations of the intensity of said spots are smaller than 40% of the wavelength $\lambda$ Another goal is to provide a vision system, referenced as a module superresolution longitudinal configured to change at least one of geometry, geometry and polarization or the polarization of a light beam emerging from a point source depending on the longitudinal position of a point source.

Another object of at least one embodiment is to provide a superresolution system for fluorescence microscopy comprising the lateral superresolution module incorporated in the illumination path of the microscope, projecting on a sample consisting of a plurality of fluorophores, positioned at different lateral positions in the compact light distribution, a sequence of light spots, of spatially differentiated size of the order of a half wavelength, each of the fluorophores fluorescing with a sequence of fluorescent light intensities depending linearly or non-linearly of the light incident on the fluorophore and characterizing a lateral position of the fluorophore.

Another object of at least one embodiment is to provide a superresolution system for fluorescence microscopy comprising the longitudinal superresolution module incorporated in the detection path of the microscope, wherein the light intensity emerging from a plurality of point sources, placed in a small illuminated volume, are separated either on separate detectors or either on distinct geometric positions on the same detector or on a combination of both.

Another object of at least one embodiment is to provide a superresolution system for fluorescence microscopy, the system comprising either a lateral superresolution module incorporated in the illumination path of the microscope, and/or a longitudinal superresolution module incorporated in the detection path of the microscope in a detection circuit for said superresolution fluorescence microscope.

Some embodiments of the present invention provide a new technique based on two optical superresolution modules, new and complementary, referenced herein as the lateral module of superresolution and. The lateral module of superresolution provides mainly additional lateral resolution and the longitudinal module of superresolution module provides mainly additional longitudinal resolution. Embodiments using a single module can also be implemented. Both optical modules are complemented by suitable algorithms and an improved detection module. The modules can be integrated into existing fluorescent microscopes. Alternatively, fluorescence microscopes dedicated and optimized can be developed around the three dimensional superresolution system.

The methods and devices for superresolution, according to embodiments of the present invention differs significantly from conventional techniques and designs of the prior art, and in so doing, provide a device developed in order to achieve the techniques and devices of a superresolution system capable of measuring with high accuracy the descriptors of a fluorophore and recognize and measure the descriptors of several fluorophores placed in the same illuminated volume.

The present invention will be better understood from the following detailed description of preferred embodiments thereof, taken together with the drawings.

Other objects and advantages of the invention will become apparent to the reader, and it is considered that these objects and advantages are part of the present invention.

BRIEF DESCRIPTION OF THE DRAWINGS

The invention will now be described in connection with certain preferred embodiments with reference to the following illustrative figures so that it can be better understood.

With specific reference now to the figures in detail, it is emphasized that the indications represented are presented as an example and for purposes of illustrative discussion of the preferred embodiments of the invention and are presented only in order to provide what is considered to be the description of the most useful and easy to understand principles and conceptual aspects of the invention.

Figure 1:
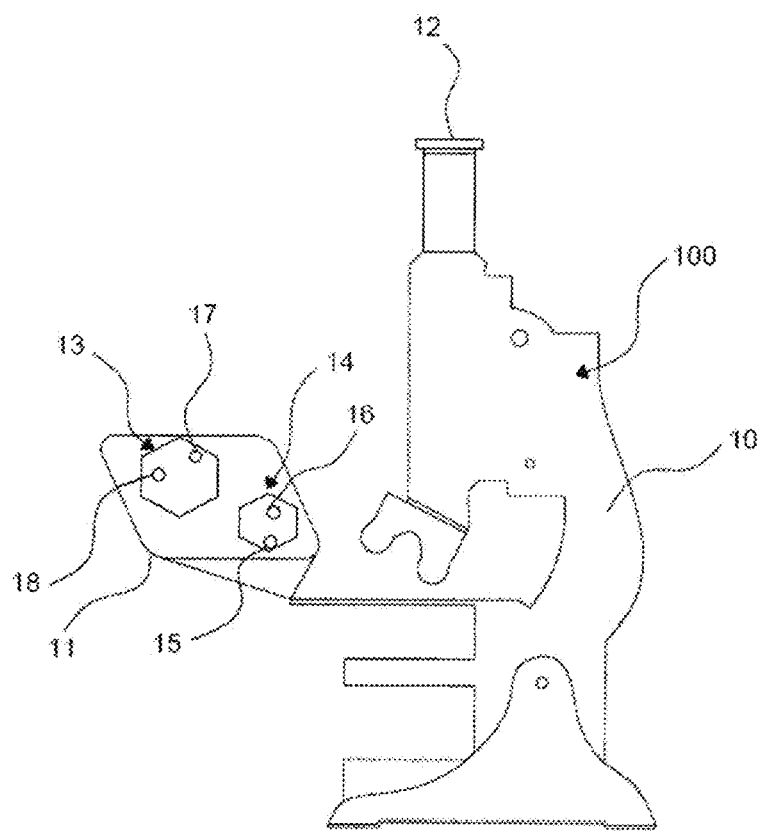

In this regard, no attempt is made to show structural details of the invention in more detail than is necessary for a fundamental understanding of the invention, the description taken with the drawings making apparent to those skilled in the art how the several forms of the invention may be embodied in practice.

Figure 2:
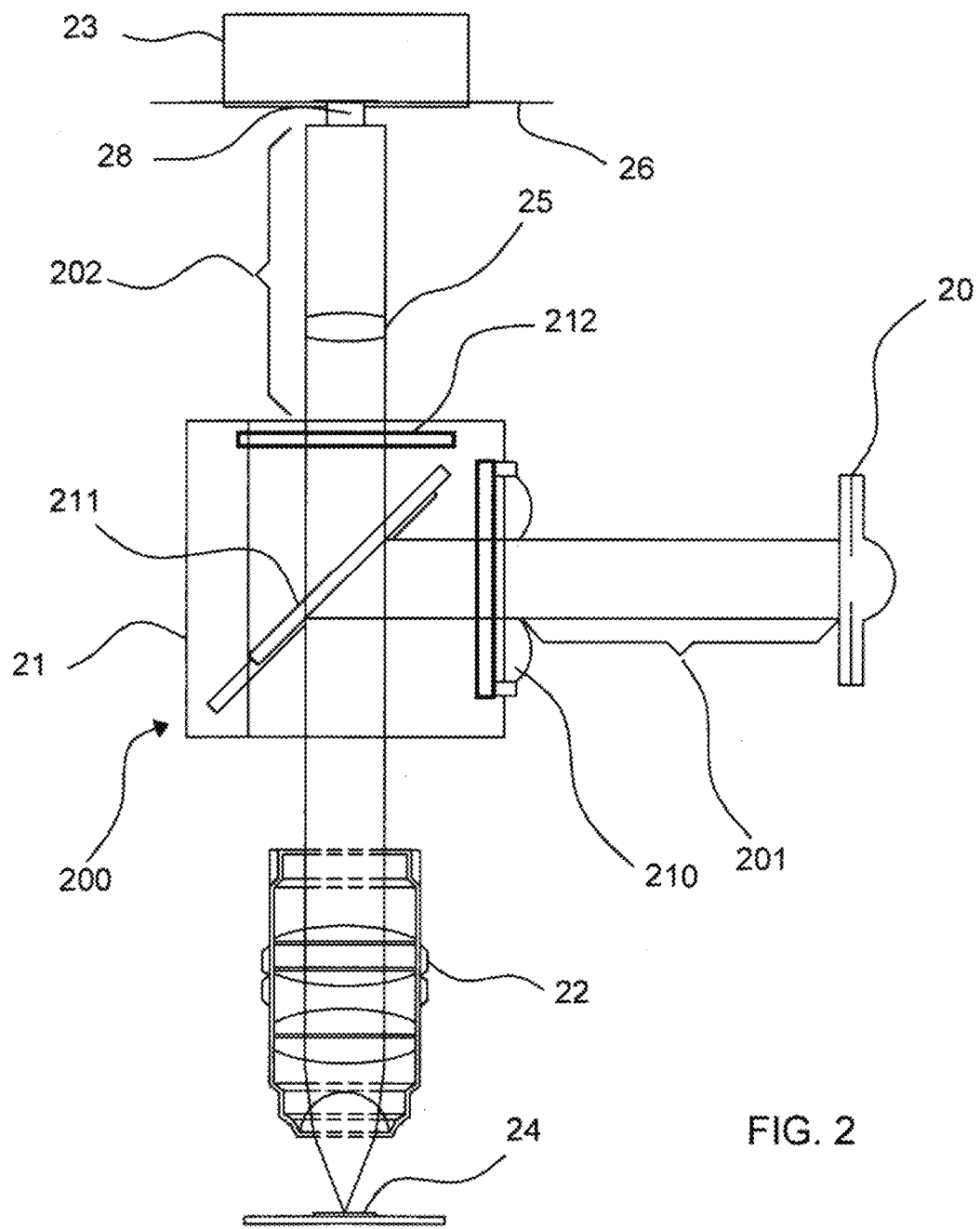
Figure 3:
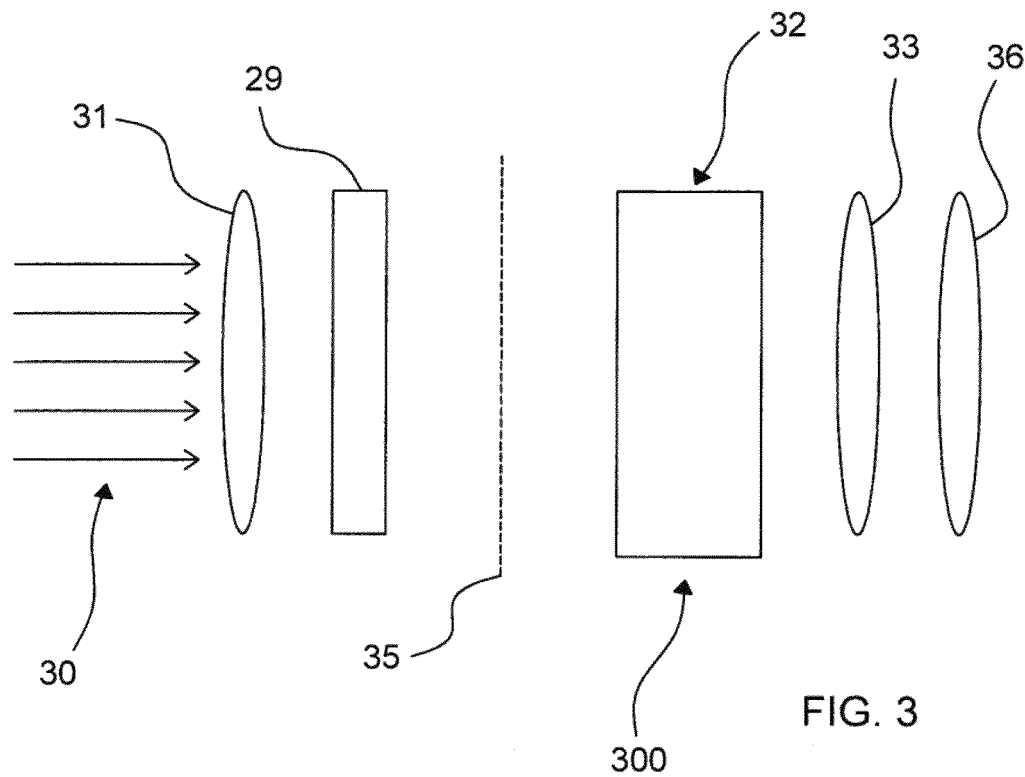
Figure 5:
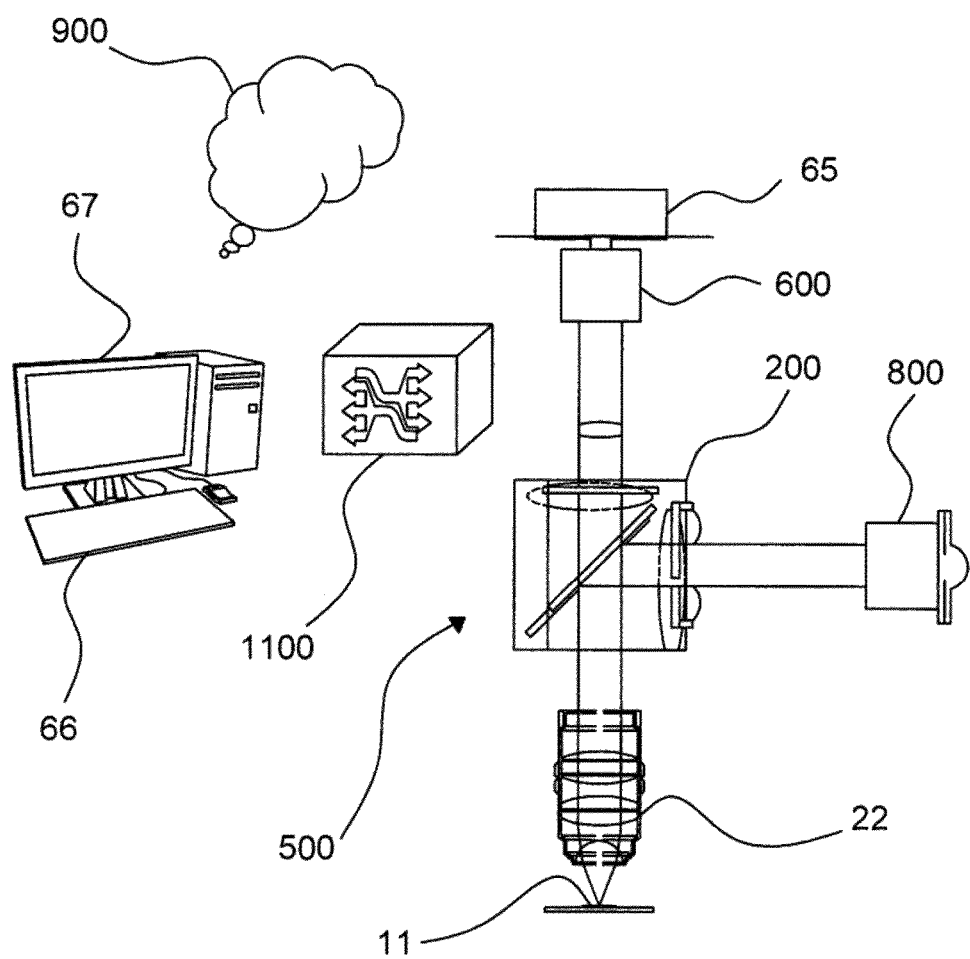

In the drawings:

FIG. 1 is a simplified perspective view of a confocal fluorescence microscope of the prior art;

FIG. 2 is a pictorial representation of a simplified superresolution fluorescence microscopy, in accordance with an embodiment of the present invention;

FIG. 3 is a simplified schematic illustration of a setup of a conical diffraction module in accordance with one embodiment of the present invention;

FIG. 4 is a simplified pictorial representation of the two measurement paradigms using confocal microscopy and methodology;

FIG. 5 is a simplified pictorial representation of the preferred implementation of the method of measurement, microscopy platform SRCDP FIG. 6 is a simplified schematic illustration of a module lateral superresolution in accordance with an embodiment of the present invention;

FIG. 7 shows tables of light distributions of a conical diffraction module according to the polarization of the polarizers of the input and output for several values of the parameter of conical diffraction, $\rho_0$. These light distributions were calculated using the software from MMresearch Corp.

Figure 8:
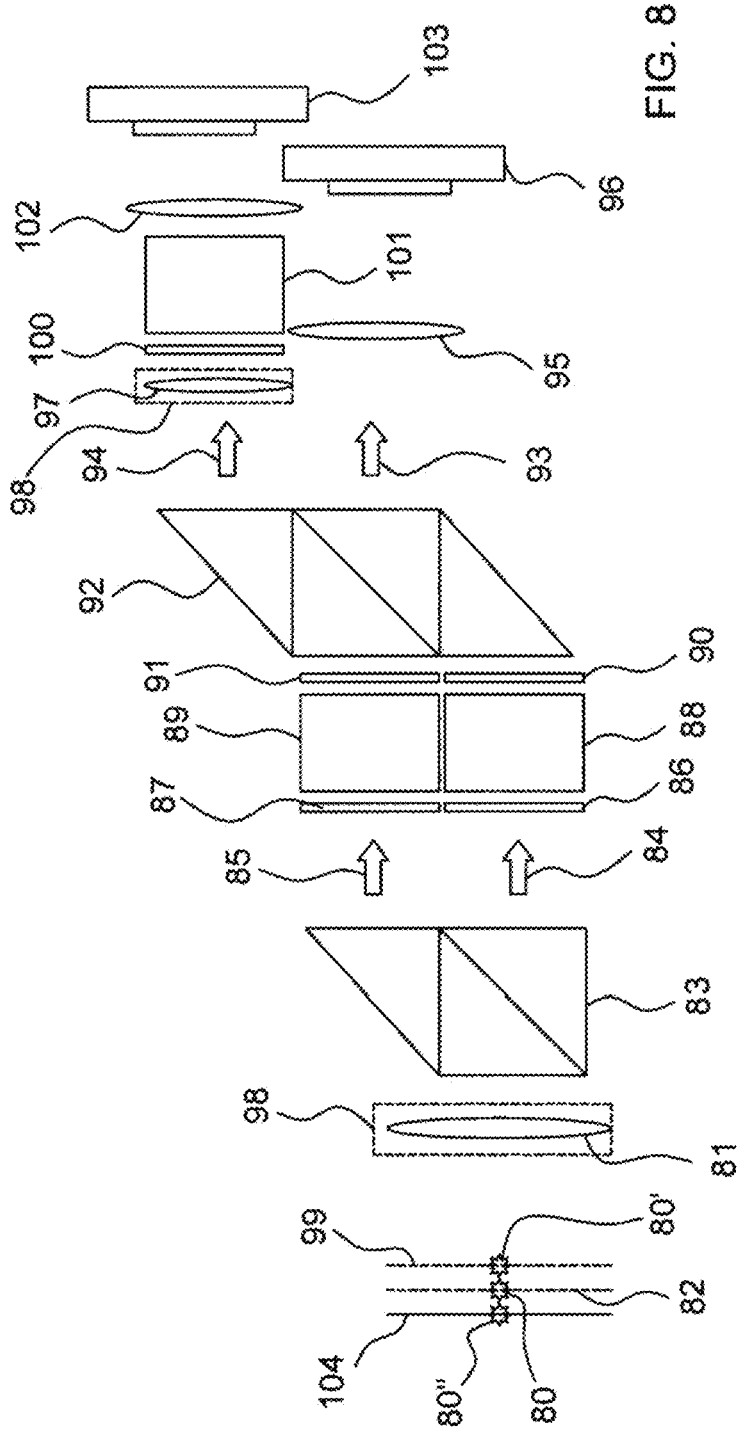
Figure 9:
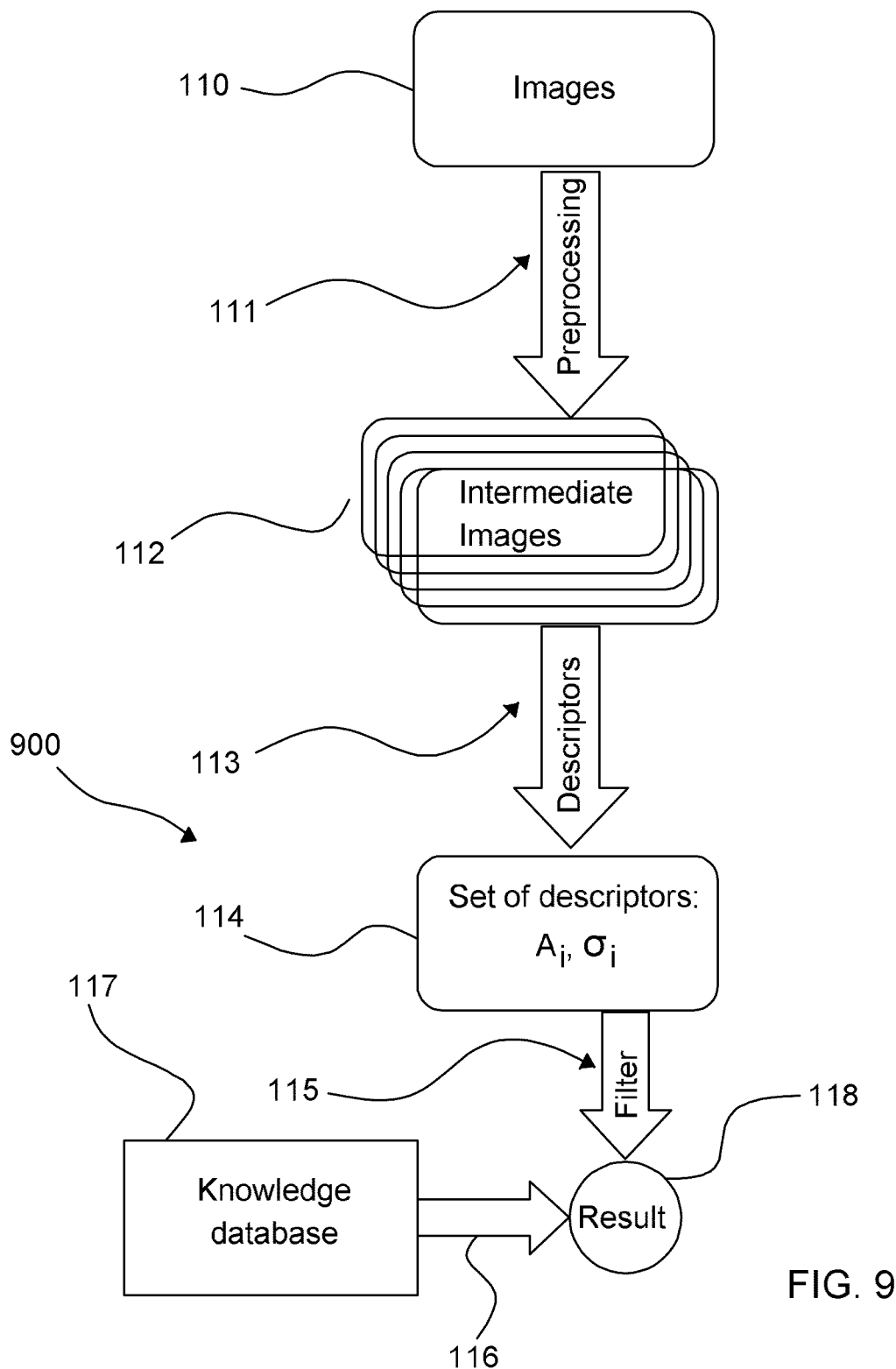

FIG. 8 is a simplified schematic illustration of a longitudinal module of superresolution in accordance with an embodiment of the present invention FIG. 9 is a simplified schematic illustration of a method for superresolution algorithm of fluorophores data, in accordance with an embodiment of the present invention.

Figure 10:
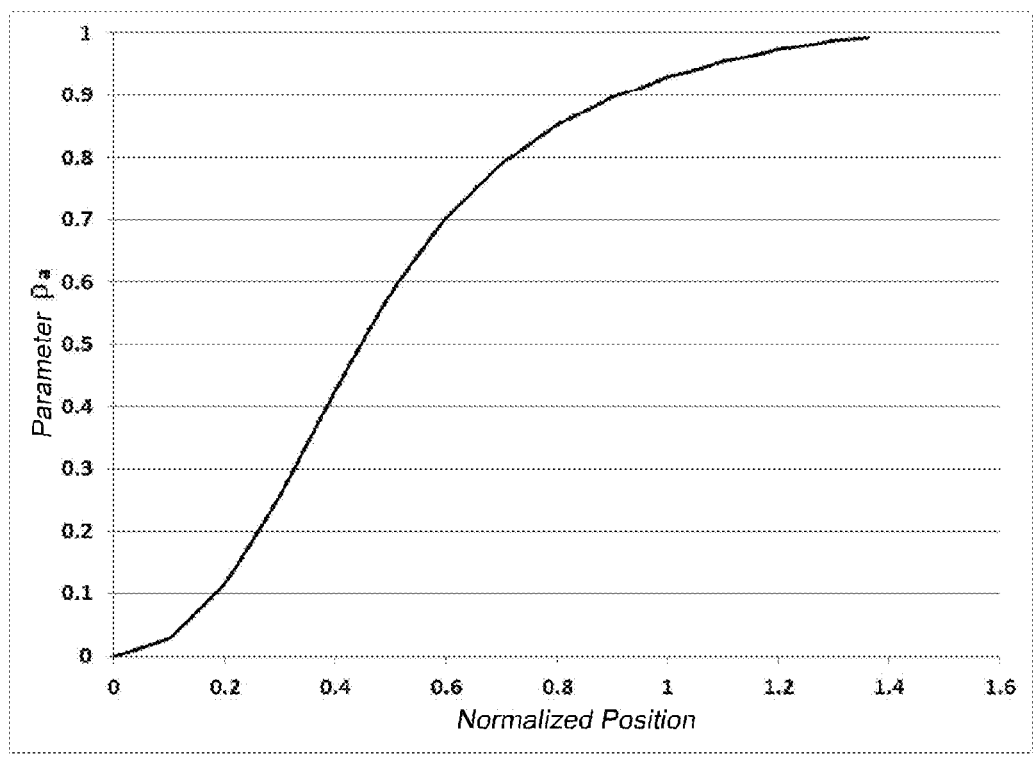

FIG. 10 is a simplified schematic illustration of the calculation of descriptors p.

FIG. 11 is a simplified schematic illustration of the control module of the platform SRCDP.

In all the figures, like reference numerals identify like parts.

DEFINITIONS AND TECHNICAL SUPPLEMENTS

The usual definitions are used for the description: phase and polarization, polarimetry, Stokes parameters and measurement techniques Stokes parameters.

The center or centroid of a light distribution is the center of gravity of the intensity. The diameter of a light distribution is the diameter of the first zero intensity, both for regular and singular waves, without taking into account the central zero of a singular wave. Two light distributions are collocated if their centers coincide or are separated by a fixed, predetermined spatial value.

In this paper we use the emission wavelength, as the basic metric system.

In this paper, the usual definitions are used for the following optical components: lens whose definition has been broadened to include all optical means which transmit, refract or reflect the light, auxiliary optics—optical sub-module to interface and adjust either the geometric parameters or the parameters of phase and/or polarization between two other optical sub-modules or modules—, polarizer, analyzer, retardation plate, beamsplitter, polarizing and non-polarizing, beam combiner, polarizing and non-polarizing.

We refer to a partial polarizer to describe a component or a module whose absorption is different for the two linear polarizations—linear dichroism—or for the two circular polarizations—circular dichroism.

We refer to dynamic sub-modules of polarization or phase, to describe the optical means, which polarization or phase vary over time in a controlled manner, discrete or continuous.

These dynamic polarization or phase sub-modules include, but are not limited to: rotating on their axes wave plate, light valves based on liquid crystal technology, electro-optical devices, also known as Pockels cells, Kerr cells, electro-optical resonant devices, magneto-optic devices, also known as cells Faraday, acousto-optic or elasto- or any combination of these means.

We refer to "centroid algorithm" to describe the standard procedure for measuring the centroid and possibly the width (FWHM—Full width Half Maximum) of a light distribution.

Many articles have been published on this algorithm such as the article Lindegren in 1978 ("Photoelectric astrometry—A comparison of methods for precise picture location," in *Modern Astrometry, Proceedings of the Colloquium*, Vienna, Austria, Sep. 11-14, 1978, 197-217 (1978)).

This algorithm has its source in Astronomy and Astrometry, and allowed the measurement of the positions of stars with high precision. This algorithm is now used throughout the optical instrumentation, including superresolution in Biology.

In this paper, the usual definitions are used for following optoelectronic components: photoelectric detector, CCD, EMCCD, CMOS SPAD—Single Photon Avalanche Diode and SPAD matrix.

We use the following terms:
- optical image for the spatial distribution of light intensity,
- electronic image to describe the spatial distribution of charges of a CCD, of current for a CMOS, of events or for a SPAD, created by the optical image, at a given moment, in a detection plane,
- digital image to describe a matrix of numbers created by conversion of the electronic image.

To simplify the reading and understanding of the text we will use the term image to the output of a single pixel detector such as PMT or SPAD, considering it as an image consisting of a single pixel.

Where no ambiguity exists, or where the distinction between the three types of images is not necessary, we will use the simplified generic term of image.

The images described in this document may be characterized as microimages, images of size substantially equal to a small number of the Airy disc diameters, typically less than 5 diameters, and/or low number of pixels, typically 4*4 to 32*32.

In a digital image Aj, the indices m and n represent the indices of the pixels, and the origin of the pixels will be selected as the projection of the center of the analysis volume defined in a later paragraph.

We presented the images using the terminology used for matrix detectors, such as CCD, EMCCD and CMOS. For SPAD and SPAD arrays the measurement result is an ordered list in time of photons impact detailing, for each photon, the time of impact and the position of the impact. To simplify the presentation of this document, we will include this case in our definition of images.

Polarimetry and Stokes Vector

Polarimetry refers to the measurement of the polarization state of incident light.

The polarization state of the incident light can be described by the Stokes parameters, a set of values introduced by George Gabriel Stokes in 1852 and used in optics.

Additional technical information known to the skilled in the art

In this chapter we take a set of technical elements necessary for the description of the invention and known to those skilled in the art.

Cartesian and Polar Coordinates

The polar coordinates of a point, $\rho, \theta$ are deduced from the Cartesian coordinates x, y using the equation:

$$\rho^2 = x^2 + y^2; \quad\quad\quad (EQ.\ 1)$$
$$\theta = \tan^{-1}\left(\frac{y}{x}\right)$$

Electric Field in Polar Coordinates and Angular Modes

Given a complex electric field vector, $E(\rho,\theta)$, described in polar coordinates $(\rho, \theta)$, the electric field can be represented by an real amplitude, $A(\rho,\theta)$, an real phase $\phi(\rho,\theta)$ and a unit vector of polarization, $u(r,\theta)$:

$$E(\rho,\theta) = A(\rho,\theta) \cdot \exp[i\phi(\rho,\theta)] u(\rho,\theta) \quad\quad\quad (EQ.\ 2)$$

It is customary in Optics to decompose the field components, i.e. its amplitude, phase and polarization in orthogonal modes, Cartesian or polar.

Many decompositions in orthogonal polar modes, such as Gaussian, Hermite-Gaussian and Laguerre-Gaussian modes are known to those skilled in the art.

We mainly use in this paper, the decomposition of the amplitude of the electric field in Hypergeometric-Gaussian modes, HyGG, with the following form:

$$A(\rho,\theta) \propto \rho^{p+|m|} \exp(-\rho^2 + il\theta) \quad\quad\quad (EQ.\ 3)$$

In this decomposition, $\rho$ is the radial mode and l is the azimuthal order.

Singular Waves

A singular wave includes a null intensity at the center and an azimuthal phase variation of a multiple of $2\pi$. This research topic in optics, initiated by the seminal article by J F Nye, et al. ("Dislocations in Wave Trains," *Proceedings of the Royal Society of London*, Series A, *Mathematical and Physical Sciences* (1934-1990) 336, 165-190 (1974)).

Topology and Compact Light Distributions

A point-source light distribution will be considered compact if it satisfies one of the conditions of compactness defined below, as two alternative and not exclusive conditions:
- either more than 75% of the energy is contained in a circle of radius less than 1.75 times the radius of Airy
- or a light domain, defined by a line of zero intensity and containing more than 65% of the energy is within a circle of radius less than twice the radius of Airy.

We distinguish different families of point light distributions, of different topologies:
- Regular distributions in their usual definition in Optics,
- Singular distributions, otherwise known as optical vortices, of topological charge (azimuthal order) i, where the phase varies from 0 to 2 $\pi$i around the direction of propagation, i being an integer,
- Amplitude distributions with azimuthal variation of order i, also referred to as Laguerre-Gaussian distribution,
- Polarization, and optionally phase distributions, with azimuthal variation of order I, referred to as radially polarized Laguerre-Gauss modes.

Two compact light distributions will be deemed being of different topological families if they meet at least one, and any of the following conditions:
- One is regular and the other is singular,
- One is point-source and the other is a ring-source
- Azimuthal orders of the amplitude of the two different light distributions differ, —
- Azimuthal orders of the polarization or the phase of the two different light distributions differ.

Alternatively, two light distributions projected onto a given volume will be considered of different topologies if a significant portion of the surface illuminated together, the gradients are of reversed direction.

The fluorophores are the best known example of the family of point-source, light nanoemitters of size substantially smaller than the diffraction limit. A nanoemitter is a small secondary light emitter attached to an object, and it is significantly smaller than a fraction of a wavelength, typically but not limited to a size smaller than one fifth of the wavelength; a light nanoemitter absorbs the incident energy and re-emits light at the same wavelength as the incident light or different wavelengths; the light emitted by the nanoemitter may be coherent, partially coherent or incoherent with the absorbed light. The main examples of nanoemitters are fluorophores and nanoparticles, but also include many other elements.

The definition in the context of the invention of nanoemitters light is determined by the following two conditions:
  Creating a secondary point-source light emitter, and
  Pre-determined positioning of the emitter with respect to a biological or organic entity.

The physical mechanisms that can create a nanoemitter are numerous, and include but are not limited to absorption, scattering or reflection, fluorescence, emission-depletion (S W Hell, et al., "Breaking the diffraction resolution limit by stimulated emission: stimulated-emission-depletion fluorescence microscopy," *Optics Letters* 19, 780-782 (1994)), photo activation phenomena (M J Rust, et al., "Sub-diffraction-limit imaging by stochastic optical reconstruction microscopy (STORM)," *Nat Meth*, 3, 793-796 (2006)), and E. Betzig, et al. ("Imaging intracellular fluorescent proteins at nanometer resolution," *Science*, 313, 1642 (2006)), fluorescence of two or more photons, W. Denk, et al. ("Two-photon laser microscopy," (Google Patents, 1991)), or non-elastic scattering, Raman scattering, or any other physical mechanisms known to those skilled in the art. We use the term light emission to describe the emission of electromagnetic waves by a light nanoemitter, the light being coherent, incoherent or partially coherent.

We extend our definition of nanoemitters by including scattering particles, absorbent or reflective, attached to a biological or organic entity; the action of a scattering, diffusing, reflecting or absorbing particle on the electromagnetic field can indeed be described, for an absorbing particle, following Babinet's principle, as a creation, with a reverse phase of an auxiliary secondary field emerging from the particle, superimposed on the incident electromagnetic field.

We refer to in this patent to descriptors of a single fluorophore to denote the set of information describing a fluorophore as a point source at a given moment. Since the nanoemitter is considered as a point source, all the information representing it contains a limited number of parameters, namely: its position in space, its intensity, its spectral characteristics of the intensity, coherence, phase and polarization of the light emitted by the fluorophore as a function of the incident light.

However, in most cases, and in the description of the invention, we refer, under the designation of descriptors, a subset of descriptors of a fluorophore including its geometric position, its intensity, and the type of fluorophore, whether several populations of light nanoemitters, differentiated for example by their emission spectrum, are present in the same sample. This simplification used in the description does not alter the scope of the invention which will include in its scope all the descriptors of light nanoemitters.

To simplify the understanding of the context of the invention, the following description refers only the simplest case, one in which the nanoemitter is a fluorophore and physical interaction is the one photon fluorescence. However, this description should be understood as a simplified illustration of a general description of the methods and concepts applicable to all light nanoemitters mentioned previously or known to those skilled in the art, regardless of the underlying physical phenomenon.

It is striking that the nanoemitter samples the incident light intensity field at a three-dimensional position accurately without influence of the complete spatial distribution of the incident intensity.

We will reference this remarkable property in this document as the sampling ability of light nano emitter.

We refer again to the FIG. 1; all fluorophores positioned on a given biological object, 16 and 19 on the one hand and 17 and 18 on the other hand, are referred to as "bright biological objects", they represent a map of the biological object, in the sense defined by Alfred Korzybski in general semantics (A. Korzybski, et al. "Une carte n'est pas le territoire: prolëgomènes aux systèmes non-aristotëliciens et à la sémantique générale" (Editions de l'Éclat, 1998)).

However, it is common practice to simplify the description, reference the object as the luminous-biological object itself, when no ambiguity can arise.

The luminous biological object contains information that is relevant to the biological object, mainly spatiotemporal information, the object position and orientation with respect to time, and morphological information, for example in the case of division of a cell in two.

The primordial Information, the map in the terminology of general semantics, is the set of descriptors fluorophores and their evolution over time. Biological and geometric information will only be extrapolations of this primordial information.

The measurement system will calculate an evaluation of the descriptors of the fluorophores, the measured map. This measured map differs from the original map, due to noise, measurement conditions, the system limits or measurement uncertainty. This information map can be developed later into different levels of abstraction.

The map, the basic level, therefore, comprises an evaluation of a set of descriptors of fluorophores, and this information may, for example, be structured as a list of fluorophores and their descriptors. This level of abstraction, which presents the results of direct measurement, contains a priori no biological information but is the results of a physical measurement described by points of light, which could also represent any marked entity.

The second level, the geometric level of abstraction, structures nanoemitters in the form of geometric objects. It comprises a description of luminous objects and their dynamic characteristics, such as their position or orientation, or their morphology. At this level, the information is still physical and geometric information describing a set of objects. The geometrical information uses the measured card and auxiliary information, potentially external to the system, the relation between light spots and objects.

The biological level of abstraction, allows some understanding of the biological reality through a constitutive relationship between objects measured and corresponding biological entities. It contains a set of information on the biological object, mainly the position and its dynamics, its shape and morphology. The biological information uses the measured card and the geometrical information and auxiliary information, potentially external to the system, the relation of the light spots and objects with biological entities. A number of conclusions on the biological functionality of the sample can be obtained at this level.

Conical refraction is an optical phenomenon predicted by W. R. Hamilton in 1832 ("Third Supplement to an Essay on the Theory of Systems of Rays," Trans. Royal Irish., Acad., pp 1-144 (1833)), and two months later confirmed experimentally by Lloyd ("On the Phenomena presented by Light in its Passage along the Axes of Biaxial Crystals", *The London and Edinburgh Philosophical Magazine and Journal of Science ii*, 112-120 (1833), and "Further Experiments on the Phenomena presented by Light in its Passage along the axes of Biaxal Crystals", *The London and Edinburgh Philosophical Magazine and Journal of Science H*, 207-210 (1833)). Conical refraction describes the propagation of a light beam in the direction of the optical axis of a biaxial crystal. Hamilton predicted that the light emerges in the form of a hollow cone of rays. Conical refraction is an important phase in the history of science and has played a role in the demonstration of the theory of electromagnetic waves.

A renewed interest in the conical refraction occurred in the last years of the twentieth century has led to a complete theory by M. V. Berry, et al. ("Conical diffraction asymptotics: fine structure of Poggendorff rings and axial spike," *Journal Of Optics A—Pure And Applied Optics*, 6, 289-300 (2004)), Berry, et al. "Conical diffraction complexified: dichroism and the transition to double refraction," *Journal Of Optics A—Pure And Applied Optics*, 8, 1043 (2006), and Berry, et al., "Chiral conical diffraction," *Journal Of Optics A—Pure And Applied Optics* 8, 363 (2006)), validated experimentally in 2009 (C. Phelan, et al., "Conical diffraction and Bessel beam formation with a high optical quality biaxial crystal," *J. Opt. A, Pure Appl. Opt*, 7, 685-690 (2009)). Here we follow the theory, terminology and definitions of Berry, including, from this point, the name change of the physical effect, using the more rigorous term of conical diffraction.

Conical diffraction has attracted considerable theoretical and experimental, but "no practical application seems to have been found," (M V. Berry, et al., "Conical diffraction: Hamilton's diabolical points at the heart of crystal optics," *Progress in Optics* 50, 13 (2007)).

Historically, conical diffraction was observed in biaxial crystals. We refer to a conical crystal to describe a biaxial crystal inorganic or organic, exhibiting the phenomenon of conical diffraction. Some non-limiting examples of biaxial crystals include Aragonite, KTP, KTA, LBO, KNb03, MDT, YCOB, BIBO, DAST, POM, NPP, LAP, and LiInS2 LiInSe2.

Other effects exist, creating inherently weaker conical diffraction effects or creating conical diffraction along a short optical path. These effects include polymers, liquid crystals and induced externally birefringence effects. The polymers include but are not limited to: stretched polymer sheets and cascade polymerization (A. Geivandov, et al. "Printable Thin Film birefringent Retarders for LCD"). Liquid crystals include but are not limited to thermotropic biaxial nematic phase (B. Acharya, et al. "Biaxial Nematic Thermotropic The Elusive Phase in Rigid Bent-Core Molecules," *Pramana* 61, 231-237 (2003)); the external effects induced birefringence include, but are not limited to applying an electric field creating an electro-optical effect on a non-centrosymmetric cubic crystal (T. Aldonado, "Electro-optic modulators," in *Handbook of Optics*, M. Bass, ed. (McGraw Hill, Orlando, 1995)); and the photo-elastic modulator (J. Kemp, "Piezo-Optical Birefringence Modulators: New Use for a Ion-Known Effect," *Journal of the Optical Society of America* 59, 950-953 (1969)).

We now refer to FIG. 3, which is a simplified schematic illustration of a configuration of a conical diffraction module 300, in accordance with an embodiment of the present invention.

Incident light, 30, is assumed to be parallel, although other conditions can be adapted using simple optical means. The setup itself comprises a first lens 31, a conical crystal 32 and an optional lens 33. The first two lenses 31 and 33 are preferably configured in the form of a Kepler telescope 1:1. The numerical aperture of the first lens 31 in the image space, represented below by $U_o$, determines the parameters of the conical [diffraction] effect through the conical radius, defined below. An imaging plane conical, 35, is placed in the focal plane of the first lens 31, a partial polarizer part 29, described above, may also be added. A focusing lens, 36, determines the scale of the final light spot. It can be a microscope objective external or can be merged with the second lens 33, as implemented in another embodiment of this invention. The distribution of the light projected onto the sample is in a first approximation, neglecting the vectorial effects, a reduced image of the light distribution in the image plane. The influence of vectorial effects will be discussed below. The scale ratio is determined for a microscope objective by the magnification.

The spatial variable, R, the conical imaging plane, and the wave vector, U, are represented by cylindrical coordinates R, $\theta_R$ et U, $\theta_U$. $\lambda$ is the wavelength of light.

The behavior of the electric field emerging from the conical crystal 32 is fully characterized by a single parameter, the radius conical Ro; the conical radius depends on the material and geometrical characteristics of the crystal, as defined in [Berry, 2004].

We introduce standardized parameters for the description below of the light distribution, to be valid in both conical imaging plane and at the focus of the microscope objective, in the limits of the scalar theory of diffraction.

The normalized radial position, $\rho$, the wave vector normalized, u, represented by cylindrical coordinates par $\rho$, $\theta_R$ et u, $\theta_U$, and the normalized radius conical $\rho_0$ are given by:

$$\rho = 2\frac{R}{\lambda}U_0, \qquad (EQ.\ 4)$$

$$u = \frac{U}{U_0};$$

$$\rho_0 = 2\frac{R_0}{\lambda}U_0.$$

$U_0$ being the numerical aperture of the system. For $\rho_0<2$, we refer here to a thin conical crystal, for $\rho_0<<1$, we refer here to the form of a linear thin conical crystal and for $\rho_0<0.5$ to a thin sinusoidal conical crystal.

The wave emerging crystal thin conical, $E(\rho, \theta_R)$, expressed in normalized coordinates, is constituted by the superposition of two waves, referred to herein as the fundamental wave, $E_F(\rho)$, a regular wave, and vortex wave, $E_V(\rho,\theta_R)$, a singular wave; these two waves are coherent one with another, collocated, and circularly polarized with an inverse direction of chirality:

$$E(\rho, \theta_R) = \qquad \text{(EQ. 5)}$$
$$E_F(\rho) + E_V(\rho, \theta_R) = E_F(\rho)\begin{pmatrix}1\\-i\end{pmatrix} + F_V(\rho)\exp(-i\theta_R)\begin{pmatrix}1\\i\end{pmatrix}$$

In this equation, $E_F(\rho)$ is the scalar fundamental amplitude, $F_V(\rho)$ is the reduced scalar magnitude of vortex and they are given by:

$$E_F(\rho)=2\pi\int du\, u\cos(\rho_0 u)J_0(\rho u);\; F_V(\rho)=2\pi\int du\, u\sin(\rho_0 u)J_1(\rho u). \qquad \text{(EQ. 6)}$$

For a thin linear conical crystal, the fundamental wave can be approximated by an Airy disk and the vortex wave can be approximated to a linear vortex, represented by:

$$F_V(\rho)=2\pi\rho_0\int du\, u^2 J_1(\rho u). \qquad \text{(EQ. 7)}$$

Assuming that the action of partial polarizer, 29, is the scaling of the vortex wave by a parameter α, the Stokes parameters can be deduced from the above equations:

$$S_0=(E_F(\rho))^2+(\alpha^2 F_V(\rho))^2$$
$$S_1=2\alpha E_F(\rho)F_V(\rho)\sin\theta_R;\; S_2=2\alpha E_F(\rho)F_V(\rho)\cos\theta_R;$$
$$S_3=(E_F(\rho))^2-(\alpha^2 F_V(\rho))^2$$
$$\beta=\theta_R; \qquad \text{(EQ. 8)}$$

We use the terms of "sparse object" to describe a set of light emitting point like emitters, of a number less than twelve, positioned in a volume whose size in each dimension is less than 3 wavelengths, at the wavelength of transmission or at the wavelength of the reflection of the emitters. The volume of a size less than 3 wavelengths that contains the sparse object is referred to as a analysis volume of reduced size.

Figure 4A:
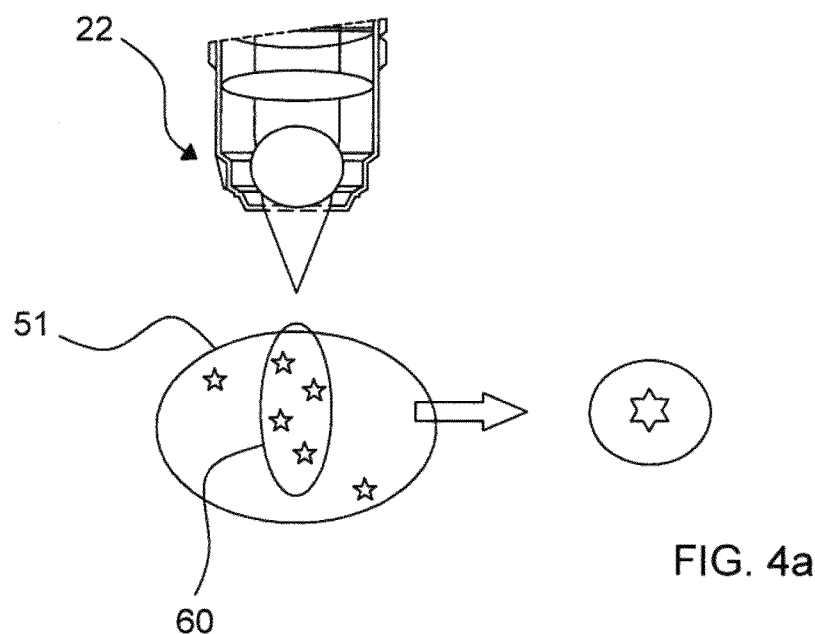
Figure 4B:
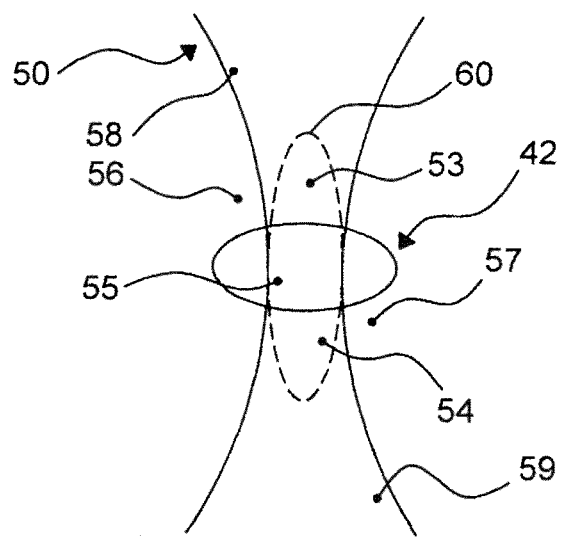
Figure 4C:
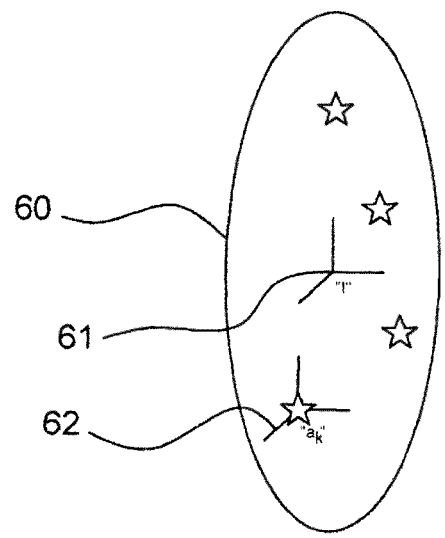

We refer now to FIGS. 4a to 4c, which are a simplified representation of the concept of volumic containment in the confocal microscope.

The functionality of the volumic containment is limited in all three spatial dimensions, the observed region of the sample volume to a size as small as possible, analysis volume. The functionality of the volumic containment limits the analysis volume by the combination of two effects: the confinement of the light projected onto a small area, ideally the size of the Airy spot, 50, and the elimination of defocused light by the confocal hole, 28, of FIG. 2. The superposition of these two effects creates a small volume, the analysis volume, 60. This volume determines the size of the elementary cell detected by the system.

Consider a sparse object, 51, consisting of a plurality of fluorophores, 53 to 59. The fluorophores from 53 to 55 positioned in the test volume 60, and only they are both excited by the light source and the photons emitted by them arrive at the detector module. The fluorophores not located in the cone of illumination, 56 and 57 are not illuminated by the incident light. The light emitted by the fluorophores 58 and 59, located at the conjugate plane of the confocal hole, 28 of FIG. 2, is blocked almost entirely by the confocal hole, 28 FIG. 2.

Two different Cartesian coordinates are defined in the system, FIG. 4c:
The reference "i": The axes referenced "i" represent a Cartesian reference system centered on the center of the analysis volume, 61.
The reference "a": the axes referenced "a" represents a Cartesian reference centered for each light nanoemitter on the nanoemitter considered as a discrete point, 62.

When using the PSIT method, described later, if a vortex is projected on the sample, the center of the vortex will be generally defined as the center of the analysis volume.

The confocal microscope limit the analysis volume using the volumic confinement described above. The volumic confinement volume is obtained by the combination of two effects: confinement of the light projected on a small surface, ideally of the size of the Airy disk, 50, and removal of defocused light by the confocal hole, 41. The superposition of these two effects creates a small volume, the analysis volume 60. This volume determines the size of the elementary cell detected by the system.

At least one embodiment of the invention uses conical diffraction to realize the fundamental optical modules of the technique. However, alternative implementations, replacing the modules based on conical diffraction by modules based on other optical concepts, are able to provide the same functionality. They are part of the scope of this invention. Alternative optical concepts include but are not limited to uniaxial crystals, subwavelength gratings, structured laser modes, holographic components and other techniques known to the skilled in the art.

These concepts, techniques and optical and optoelectronic devices are known to those skilled in the art and all such optical means are described in numerous publications such as the book written by D. Goldstein, et al. ("Polarized Light" (CRC, 2003), Vol. 83). The "Handbook of Microscopy Confocal", J B Pawley, (Springer Verlag, 2006). "Handbook of Optics", M. Bass, (McGraw-Hill, 2001)) and many other publications known to those skilled in the art.

Acronyms

We use in this paper the acronym, SRCD, "Super Resolution using Conical diffraction" to name the platform, modules and systems specific to the preferred implementation of this invention.

We use in this paper the acronym PSIT "Projected Sequence of Intensities with various topologies"

We use in this paper the acronym, PDOS, "Position Dependent Optical Semaphore".

The SRCDP platform, "Conical diffraction using Super Resolution Platform" is a platform for microscopy, implementing the measurement methodology and using optical modules based on conical diffraction.

SRCDP platform is the preferred implementation of the measurement methodology. We use in this paper the acronym LatSRCS to name the optical module implementing the PSIT method for the preferred implementation of this invention.

We use in this paper the acronym LongSRCS to name the optical module implementing the preferred implementation of the method PDOS of this invention.

Some embodiments of the present invention comprise a new measuring methodology; the measurement methodology, and a coherent set of systemic and algorithmic method, hardware tools, software tools and algorithms for its implementation The measurement methodology according to embodiments allows acquisition of nanosized optical data and image superresolution.

The measurement methodology is primarily, but not exclusively, used for the measurement of super-resolved biological samples data marked with fluorophores.

The measurement methodology can be implemented using the different methods of measurement and processing algorithms, described below.

Among other things, the measurement methodology can be implemented together or separately using two new measurement methods, referred to as:

PSIT Projected Sequence of Intensities with various Topologies," and

PDOS, "Position Dependent Optical Semaphore".

Some embodiments of the invention also relate to a system—a platform for microscopy—implementing the methodology of measurement using the measurement methods PSIT and PDOS. This system, the SRCDP platform, "Conical diffraction based Platform Super Resolution" is the preferred implementation of the measurement methodology.

The SRCDP platform comprises mainly two hardware modules, two new and complementary optical modules the LatSRCS and LongSRCS optical modules, mounted on a microscope, and an algorithmic module SRCDA, to reconstruct the information of the sample superrésolue.

Additionally, the SRCDP platform includes an improved detection module, a control module of the system, and software support.

The measurement methodology comprises using both measurement methods, the methods PSIT and PDOS. However, in some applications, the use of both methods may not be necessary, we will refer in this case to the simplified measurement methodology, which is part of the scope of this invention.

Some embodiments of the invention also relate to methods of using the measurement methodology for measuring distribution of fluorophores and fluorophores, and monitoring in two or three dimensions of fluorophores.

In addition, certain embodiments of the invention relate to a large number of variants of implementations of the methodology and methods PSIT and PDOS, platform SRCD, optical modules and LatSRCS LongSRCS and algorithmic SRCDA.

The functionality of the confocal microscope described by M. Minsky ("MicroscopyApparatus," (Google Patents, 1961)) and explained previously, is limiting in three spatial dimensions, the observed region of the sample volume to a size as small as possible, the volume analysis.

As a corollary, in a confocal fluorescence microscope, the information retrieved is a single value of intensity for the entire volume analysis, considered as a single entity. More clearly, detailed information on the position of fluorophores within the analysis volume is not available, a priori, in a confocal microscope. It was generally agreed that no additional optical information could be created that would allow further discrimination within the illuminated volume.

Figure 4D:
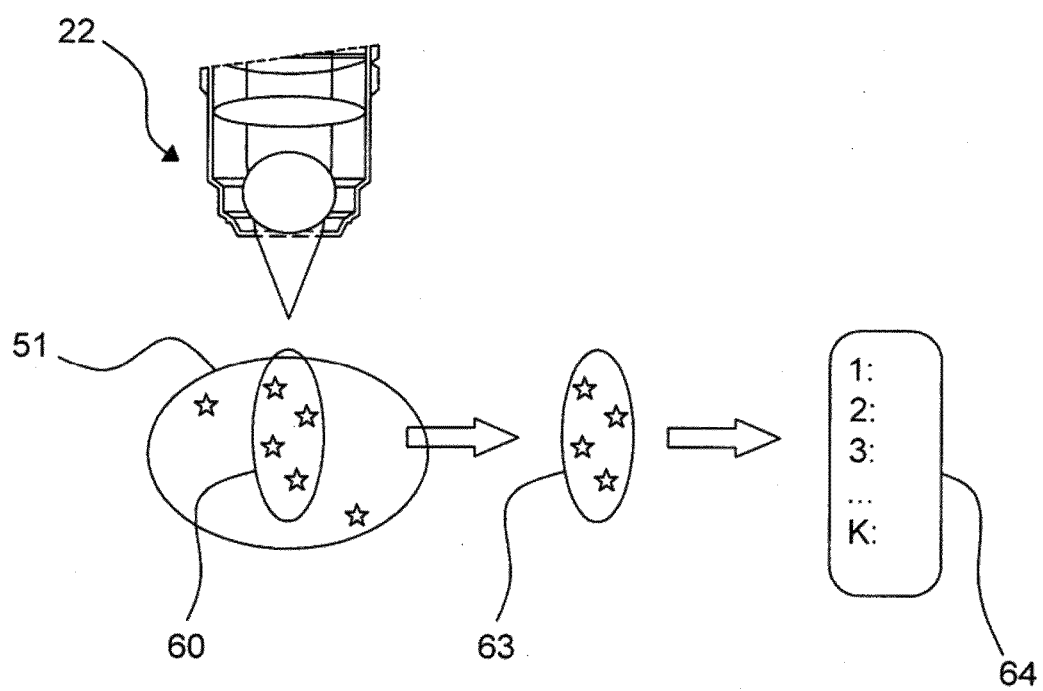

Referring now to FIG. 4d, which is a simplified conceptual representation of the paradigm of the measurement methodology according to at least one embodiment of the invention. The paradigm of this methodology is much more ambitious than that of the fluorescence confocal microscope, shown schematically in FIG. 4a.

In FIG. 4d, a test volume 60 is created at the focal plane of the microscope objective, 22; it contains a sparse object, 51, consisting of several fluorophores, 53 to 59; the result of the system implementing the method is a reconstructed sparse object, 63, a list of fluorophores and a list of their attributes, 64.

A system implementing the method according to at least one embodiment of the invention is capable of recovering independently and accurately the attributes of several fluorophores in a luminous volume of dimensions similar to those of confocal microscopy. To achieve this goal, the methodology according to some embodiments of the invention is designed to create optically for each illuminated volume, a large amount of information in both time and spatial domains.

The most developed process of the measurement methodology, according to an embodiment of the invention, can be segmented into seven steps, five optical steps, an optoelectronic detection step and an algorithmic step.

Optical Steps:
    Projection of a sequence of compact light distribution of different topologies on the analysis volume
    Emission of fluorescent light by fluorophores
    Imaging of fluorophores in the focal plane
        Separation of the reflected light detected in several independent channels simultaneously and/or sequentially
        Optional limitation in the focal plane of the analyzed light Detecting Step
    Detecting the light intensity by one or more point like or matrix photodetectors.

Algorithmic step:
    Reconstruction of the list of fluorophores, constituting the sparse object, and their attributes from the set of the detected images, According to another embodiment of the present invention, the measurement methodology consists in the realization of optical steps, previously described and omitting either the first is or the fourth optical step.

The compound optical process that implements the methodology comprises: performing a series of optical measuring processes, controlled by the control module of the system, by varying the sequence of illumination and/or the functionality of the channels and/or the position of the sequence illumination as function of measured data or of external information. An example of compound optical process implementing the methodology according to an embodiment of the invention will be detailed below.

The intermediate result, the raw information is obtained at the end of the detection step. Raw information comprises a set of images $A_{op}(m, n)$ representing for the o light distribution, the image from the detection channel p.

As in a confocal microscope, the measurement process analyzes a small volume in a much larger object. It will therefore require the addition of additional modules, similar to those of a confocal microscope including a scanning process, a software module integration, analysis and visualization of data points in surfaces and/or three-dimensional objects.

A method of measurement PSIT according to one embodiment of the invention, projects a sequence of light distributions of different topologies, on the analysis volume.

The measurement method PSIT, performs the following functions:
    Projection of a sequence, the emission sequence of compact light distributions of different topological families on a sample, and
    For each compact light distribution:
        Emission of light by fluorophores on the sample,
        Creation, by means of the microscope optics, of an optical image,
        Acquisition of the optical image on a photodetector and creation of a digital image.
    In more detail, it is noted that:
    The transmission sequence comprises at least two point like light distributions, of different topological families The transmission sequence is projected onto a biological sample labeled with fluorophores which are referenced as light nanoemitter.

The light emitted, emerging from each light nanoemitter, is dependent for each nanoemitter of the light intensity, in the incoherent case or on the electromagnetic field, in the coherent case, incident on the three-dimensional spatial position of the light nanoemitter, the aforesaid light sampling property of the nanoemitter discussed previously.

For each light distribution pattern of the transmission sequence projected on the sample, an optical image is created.

The set of images corresponding to all the light distributions of the transmission sequence is referred to as the sequence of images.

The PSIT method according to this embodiment can acquire mainly lateral information, that is to say, the lateral position of each of the fluorophores.

In a preferred embodiment, the PSIT method is implemented by the projection of light distributions of different topologies created by conical diffraction and modified by a variation of the polarization states of input and output.

A PDOS method according to an embodiment of the invention includes the distribution of an "optical semaphore" of the light reemitted by the fluorophores between at least two detectors.

Ideally, the function of the optical semaphore is to separate different areas of the test volume on different detectors. Practically, the optical semaphore creates, for each detector, a transfer function of the light emitted by a light nanoemitter, depending on the position in space of the light nanoemitter and different for the different detectors.

In a preferred embodiment, the PDOS method is implemented to separate on different detectors the collimated light, emerging from fluorophores positioned at the focal plane of the lens, from non-collimated light emerging from fluorophores lying within or beyond the focal plane.

The PDOS method, in its preferred embodiment, allows acquiring essentially longitudinal information, that is to say, the longitudinal position of each of the fluorophores.

Mathematically, the method according to some embodiments of the invention provides a transfer function converting the spatial distribution of the fluorophores in space in unprocessed information consisting of a set of images. The algorithmic performs the inverse operation: it reconstructs the spatial distribution of the fluorophores in space from the set of images in the unprocessed information.

In mathematical terms the algorithm solves an inverse problem or parameter estimation. The model equations are known and the number of fluorophores in a sparse object is a-priori limited. 11 the mathematical procedures known to those skilled in the art can be used for solving inverse problems and parameter estimation. We describe later an example of algorithm adapted specifically to the measurement methodology according to an embodiment of the invention.

In addition, we present, for its symbolic value, a new solution to the problem of discrimination of two points located at a small distance from each other. This problem studied by Lord Rayleigh, is the base of the resolution criterion in many areas of Optics.

It has thus been described, rather broadly, the characteristics of the invention in order that the detailed description thereof may be better understood, and in order that the present contribution to the art may be better appreciated. Many additional features of the invention will be described below.

The preferred implementation of the method according to one embodiment of the invention is a hardware platform and algorithms, referred to as the SRCDP platform, 500, shown in FIG. 5.

The SRCDP platform, 500, implements the method according to an embodiment of the invention, by combining the two methods PSIT and PDOS above.

The platform SRCDP observed, FIG. 5, a biological sample, 11, including a plurality of fluorophores. The result of the observation of the biological sample by the SRCDP platform is the acquisition of superresolution information, representative of the observed sample.

The platform SRCDP, 500, FIG. 5 includes mainly:

In its Hardware Part:
  A confocal microscope 200, adapted or optimized, similar to the confocal microscope, described previously, and including all appropriate components, as previously described
  Two new and complementary optical modules, mounted on a standard microscope. The two new optical modules are optical modules LatSRCS, 700, and LongSRCS, 800, described in detail later with reference to FIGS. 6 and 8, respectively. The optical module 700 LatSRCS, implements the steps of illumination required for implementing the PSIT method according to one embodiment of the invention. The optical module LongSRCS, 800, implements the steps of the light intensity distribution in a plurality of emerging Images of the PDOS method according to an embodiment of the invention and;
  Module algorithmic SRCDA, 600, which will be described by referring to FIG. 8, is able, to reconstruct superresolution information of the biological sample from images created by the platform SRCDP.
  Other auxiliary elements, such as computer 66 and software 67, necessary for the realization of the platform,
LatSRCS Optical Module Implementing the PSIT Method We describe, with reference to FIG. 6, an optical module according to an embodiment of the invention, the optical module LatSRCS, 700, and its specific function in microscopy.

The optical module LatSRCS, 700 according to this embodiment is an optical module, projecting on a plurality of fluorophores in a sample, a sequence of compact light distributions of different topology. Each fluorophore fluoresces with a sequence of fluorescent light intensities dependent on the incident intensity on the fluorophore and characterizing the lateral position of the fluorophore. In most embodiments, the light compact distributions of different topologies are created by interference with variable amplitudes and phases between an ordinary wave and singular wave. In the preferred embodiment, the regular and singular waves are created by a thin conical crystal.

The optical module LatSRCS, 700, is positioned in the illumination path of the confocal microscope 200; it projects a sequence of compact light distributions of different topologies on the sample 11 using the confocal microscope objective 200. In the preferred embodiment using the conical diffraction, the incident intensity at a specific position on the sample 11 will be proportional for each light distribution pattern, to a specific combination of the Stokes parameters.

The optical module LatSRCS, 700, uses an inherent feature described above, specific to the fluorophore, which samples the intensity of light incident on its precise position (the fluorophore), and reemits fluorescent light dependent on the incident light. It is remarkable that the measured information is directly related to the position of the fluorophore in the compact light distribution, relayed by the Stokes parameters. This information is frozen by the functionality of the fluorophore, its ability to absorb and re-emit light, breaking the optical chain. This information is carried by the fluorescent light as an emerging light distribution recoverable by a detector assembly 65.

If the incident light varies temporally according to a sequence of compact light distributions of different topologies, the intensity of the fluorescent light reemitted varies in the same proportions. The sequence of the re-emitted fluorescent light is proportional to the sequence of compact light distributions of different topologies. From this information, it is possible to retrieve the position of the fluorophore, as explained below.

The PSIT method, according to embodiments of the invention, refers to the projection of a sequence of compact light distributions of different topologies in a microscope, the interaction with fluorophores, collecting the reflected light by the objective of microscope, 22, detecting the fluorescent light by the improved detector assembly 65, and the analysis of the information by a suitable algorithm. In some embodiments, the improved detection assembly, 65, comprises a single detector, and recovers only the overall intensity as a function of time, while in other embodiments the improved detection assembly comprises a small area of pixels and recovers also the spatial distribution of the fluorescent light. All retrieved information consisting of a plurality of images, the named as lateral superresolution images.

In a preferred embodiment, the contribution of a fluorophore in the illuminated volume positioned in a specific lateral superresolution image is proportional to a specific combination of the Stokes parameters of the incident light at the fluorophore position.

Lateral superresolution images, the information created by compact light distributions of different topologies, is new and was not present in the prior art. This new information helps to refine the position of the fluorophores, to quantify the number of fluorophores present in the illuminated volume and to differentiate multiple fluorophores present in the same volume.

We refer now to FIG. 6, which is a simplified schematic illustration of an optical module LatSRCS, 700 in accordance with an embodiment of the present invention.

FIG. 6 shows an optical module LatSRCS, 700; it includes all the components of the module of conical diffraction, of FIG. 3, which are implemented in the same way as in the module 300 of conical diffraction. The optics of the light source of the scanning confocal microscope is assumed to be infinite conjugate, although other conditions can be adapted using auxiliary optics. The incident light entering from the light source is parallel, 30. The optical module itself, 700, comprises a first lens 31, a conical crystal 32, and a second lens 33; a partial polarizer, 29, described above, may also be added. The first two lenses 31 and 33 are preferably configured in the form of a Kepler telescope of ratio of 1:1; the conical imaging plane, 35, is placed in the common focal plane of the lenses 31 and 33. The numerical aperture of the first lens, 31, determines the parameters of the conical diffraction effect through the conical normalized radius, defined below. The second objective 33, restores the parallelism of the light, to inject it in the microscope. It further comprises a sub-module of polarization control 71, including, for example, a rotating quarter-wave plate, a pair of liquid crystal light valves or a Pockets cell, 72 and an analyzer 73. The information of the Stokes parameters can be converted into sequence information, through a sequence of light distributions spatially differentiated and carrying sequential information, as described above.

Figure 7A:
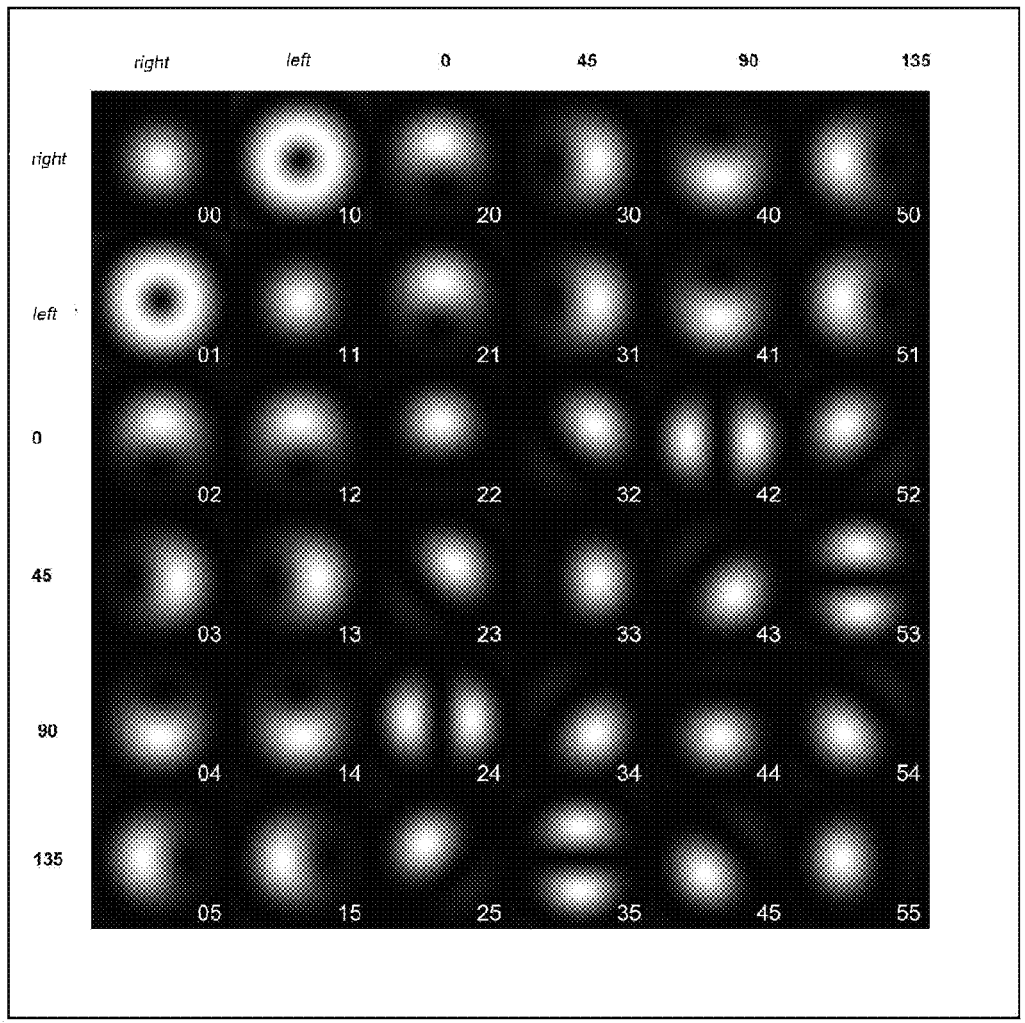

Referring to FIG. 7a, this figure shows the light distribution, created through a conical crystal with a normalized conical parameter $\rho_0$ of 0.388, calculated by a scalar approximation for different input and output polarization states. These light distributions were calculated using the software Diffract from MMresearch Company. These light distributions were calculated in an imaging intermediate plane and not at the focus of the objective to separate the conical refraction [should be diffraction] effects from vectorial effects. The—input and output—states of polarization are characterized by their angle for linear polarizations and their chirality for circular polarizations.

Figure 7B:
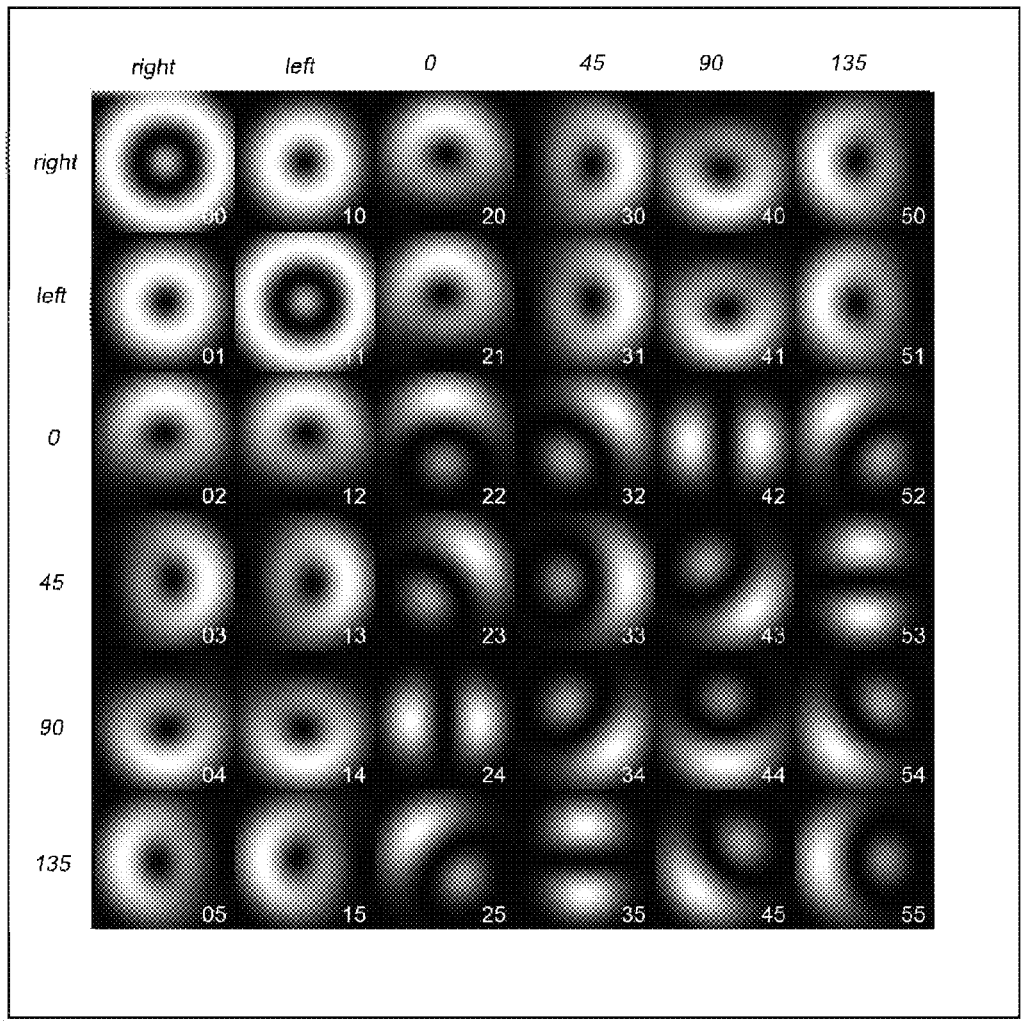

Referring to FIG. 7b, this figure shows the light distribution, created through a conical crystal with a normalized conical parameter $\rho_0$ of 0.818, calculated by a scalar approximation for different input and output polarization states. These light distributions were calculated using the software Diffract from MMresearch Company. These light distributions were calculated in an imaging intermediate plane and not at the focus of the objective to separate the conical refraction [should be diffraction] effects from vectorial effects. The—input and output—states of polarization are characterized by their angle for linear polarizations and their chirality for circular polarizations.

We denote mainly the following light distributions:
The fundamental, FIG. $7a_{00}$ and FIG. $7a_{11}$ obtained between parallel circular polarizers, which is a distribution close to the Airy distribution,
The vortex: FIG. $7a_{01}$ and FIG. $7a_{01}$ obtained between crossed circular polarizers,
The distribution that we called the "crescent moon" distribution; the subfigures $7a_{0,2\text{-}5}$, $7a_{1,2\text{-}5}$, $7a_{2\text{-}5,0}$ et $7a_{2\text{-}5,1}$, are obtained between a circular polarizer and a linear polarizer with a variable angle. This distribution is antisymmetric and the axis rotates following the linear polarizer axis,
The distribution that we called the "half-moons" distribution; the subfigures FIGS. $7a_{42}$, $7a_{35}$, $7a_{24}$ et $7a_{53}$ are obtained between two crossed polarizers; this distribution is symmetric,
The more complex light distributions, FIG. 7b, for a crystal with a normalized conical parameter, $\rho_0$, greater than 0.5,
The creation of additional light distributions using two—or more—crystal cascading conical crystals (not shown) with or without static or dynamic polarizing elements between the crystals.

Redundancy and Random Phase Variations

The elementary light distributions described in FIG. 7 can be obtained in several ways. In addition, some of them can be obtained as a linear combination of other elementary light distributions, e.g. the vortex can be obtained by the sum of any two orthogonal "half-moons" light distributions.

This redundancy allows some averaging of random phase errors inevitably present in many measurement process of biological objects. This reinforces the robustness of the measurement methodology of the embodiments of the invention and its applicability.

New light distributions can also be obtained as mathematical combinations of elementary light distributions. The "pseudo-vortex", light distribution, calculated from arithmetic combinations of the four distributions Stokes has the feature of having a strong gradient at the origin.

Method PS1T was originally designed to allow lateral superresolution, however PS1T method can also be used to obtain the longitudinal position of a fluorophore. Indeed, some elementary light distributions are relatively insensitive—within reasonable limits—to a variation of the longitudinal position of the fluorophore, others are rather sensitive. A sequence of compact light distributions, some of them independent and some of them depend on the longitudinal position would reveal the longitudinal position of fluorophores.

In addition for the light distributions which are highly dependent on the longitudinal position of the fluorophore, a series of elementary light distributions slightly shifted longitudinally, one relative to the other can be projected on the sample, allowing a set of images containing longitudinal information.

In addition, some more complex elementary light distribution, consisting of more complex overlapping of waves with a strong longitudinal dependence exist, eg the "three-dimensional dark spot" described by Zhang ("Generation of three-dimensional dark spots with a perfect light shell with a radially polarized Laguerre-Gaussian beam," *Applied optics*, 49, 6217-6223 (2010)), which create a black spot surrounded in three dimensions by a luminous sphere. These "three dimensional dark spots" consist of a superposition of Laguerre-Gauss functions, which can be achieved within a laser cavity or using a hologram or a phase plate, as suggested by Zhang, or using uniaxial or conical crystals as suggested by the inventor.

All these variants of the measurement methodology are considered part of the invention. The inventor has yet chosen in the preferred implementation to separate in two optical modules, disjoint but complementary, lateral measurement and longitudinal measurement to reduce the complexity of each of the modules.

Vector Effects

The theory developed so far describes the light distribution in the imaging plane of the microscope 35. The distribution of the light projected onto the sample is, according to the theory of the geometrical imaging, a reduced image of the light distribution in the image plane.

However, as described extensively in the literature, for a high numerical aperture objective, the imaging geometric theory is not accurate and vector effects must be taken into account. These effects consist essentially in the presence of a component, longitudinally polarized.

Referring again to FIG. 6, to mitigate vector effects, it may be advantageous to maintain the final analyzer fixed and to add an additional element, fixed or variable, the output polarization adaptation submodule, 74, for controlling the output polarization. We found that an output polarization with circular symmetry greatly reduces the effects vector. Such polarization can be circular, radial or azimuthal. For circular polarization, the output polarization adaptation submodule, 74, is simply a quarter wave retardation plate. In this case, the elements of longitudinal polarization have vortex symmetry and integrate harmoniously into the system with only a small change in the form of the Stokes parameters, even for microscope objectives with high numerical aperture.

Alternatively, the output polarization adaptation submodule, 74, may be variable and adapted to the topology and the symmetry of each of the compact light distribution.

LongSRCS Optical Module Implementing the PDOS Method

We describe below an optical module LongSRCS with more details. The system of longitudinal superresolution, according to an embodiment of the invention, channels the incident light intensities of a plurality of point sources located in a small illuminated volume, either on separate detectors or on distinct geometric positions on the same detector or on a combination of both, as function of the spatial position of each point source.

In simpler words, the intensity emitted by a fluorophore positioned longitudinally at the point A will be physically separated from the intensity emitted by a fluorophore positioned longitudinally to point B.

The optical module LongSRCS, according to an embodiment of the invention, allows the separation in volume slices, different slices of the illuminated volume being physically separated on different sets of detectors.

In the preferred embodiment, which will be explained below, the optical module LongSRCS separates an illuminated volume in at least three adjacent slices, separating the middle slice from of the other two slices on sets of independent improved detectors, and creating a spatial differentiation between the two remaining slices on the same set of improved detectors.

We refer now to FIG. 8, which is a simplified schematic illustration of a LongSRCS optical module, 800, according to an embodiment of the present invention.

The optical module LongSRCS channels the incident light intensity of a plurality of point sources located in a small volume of light, either on separate detectors or on distinct geometric positions on the same detector either a combination of both, depending on the longitudinal position of each point source.

In a preferred embodiment, it operates on the fluorophores, represented by 80, 80' or 80", according to their longitudinal position. It comprises a first collimating lens 81, which may consists, in some embodiments of the microscope objective 4.

The fluorophore 80 is positioned in the focal plane of the collimating lens 82, the light from the fluorophore 80, emerging from the collimating lens 81 is collimated.

The fluorophores 80' and 80" are placed before and after the focal plane of the collimating lens, 82, at a distance of $\pm\Delta z$, the light from the fluorophores 80' or 80" emerging from the collimating lens 81 being convergent or divergent.

The LongSRCS optical module includes a polarization beam separator, shown in FIG. 8, in the form of a lateral displacement polarization beam splitter, 83. The polarization beam splitter splits the incident light, assumed to be non-polarized in two polarization channels, 84 and 85, having orthogonal linear polarizations. The system can be simplified by using a single polarization channel instead of two, if the incoming light is already polarized or at the cost of a loss of half of the intensity of the incident light, for unpolarized light.

Two quarter waveplates, 86 and 87, transform, for each channel, the linearly polarized circular polarizations.

A conical crystal is placed in each of the channels 88 and 89. In each channel, a conical diffraction setup, as described in the FIG. 3, is constituted by the collimator lens 81, acting as a primary objective of the setup of conical diffraction, 31, and a conical crystals, 88 and 89. Conical diffraction pattern will be complemented by a second lens 33, in the following.

For the fluorophore, 80, positioned in the focal plane of the collimating lens 82, the light emerging from the collimator lens 81, is, as discussed above, collimated; referring to the setup of conical diffraction, the Numerical Aperture of the collimating lens 81, in the image space, and [so] the normalized radius cone are zero, so that the effect of conical diffraction on the beam from the fluorophore 80 is zero. Therefore, the conical crystal does not change the geometry of the fluorescent light emitted by the fluorophore, or its polarization, which remains circular with the same chirality.

For fluorophores, 80' or 80", which are not positioned in the focal plane of the collimating lens 82, the light diverges or converges; Referring again to setup conical diffraction described above, the Numerical Aperture in the image plane of the collimating lens 81, which is equivalent to the first lens of the conical diffraction setup, 31, is non-zero. For a given value $\Delta z$ defocus, positive or negative, most of the light emerging from the crystal is contained in the conical wave vortex, which has a form of a vortex, and is inverted chirality.

The functionality of the conical diffraction setups positioned in each of the channels is to distinguish the collimated light from the light converging or diverging by reversing the chirality of the circular polarization of the light for converging or diverging light.

Two other blades quarterwave plates, 90 and 91 transform the circular polarizations, emerging each channel, linear polarizations. We refer, for each channel, to the linear polarization, which would have emerged from the retardation plate, if the crystal had been removed, as the polarization of collimation The optical module comprises a LongSRCS combiner/separator of four ports, shown in FIG. 8 as a lateral separation four ports combiner/separator 92.

For each channel it separates the two polarizations, and merges the two polarizations of collimation in the same path, the path of collimation, 93, and the polarized light orthogonal [to the collimation polarization] in another path, the path of non-collimation, 94. The directions of the axes of the quarterwave plates, 86, 87, 90 and 91 must be chosen appropriately. The combined beams do not interfere, because they come from originally unpolarized beam.

The incident light into the path of collimation is focused onto the detector of collimation, 96, using the focusing lens of the collimating path, 95, which behave functionally as the second lens, 32, of the conical diffraction setup.

In the path of non-collimation, an additional lens 97 is inserted, and the additional lens 97, together with the collimating lens, 81, creates a new lens system, 98, whose focal plane, 99 is positioned at a different position of the focal plane of the collimating lens 82, the position of the fluorophore 80'. An additional quarter waveplate, 100, cancels the action of the quarter waveplates, 90 or 91, turning back the incoming beams of each of the channels of polarization, to the circular polarization, which they were at the output polarized crystals conical, 88 or 89.

An additional conical crystal, 101, is added in the way of non-collimation as a third conical diffraction setup—the auxiliary conical diffraction setup—with the system of lenses 98, acting as the first lens of the conical diffraction setup, 31.

The fluorophore 80' have been positioned before the focal plane of the collimating lens, 82, at a distance of Δz, but, relative to the lens system 98, it is positioned at the focal plane 99. The light from the fluorophore 80' had already been converted into a vortex by one of the conical diffraction setups consisting of the collimating lens 81, and one of the conical crystals 88 or 89, depending on the channel of polarization traveled by the light. The light from the fluorophore 80 is collimated at the output of the lens system, 98, after the additional lens, 97.

Referring to the new conical diffraction setup, the numerical aperture of the lens system in the image space, and the normalized conical radius are zero for fluorophore 80; the effect of conical diffraction, of the auxiliary diffraction setup, on the beam emerging from fluorophore 80 is zero. Therefore, the conical crystal does not change the geometry of the fluorescent light emitted by the fluorophore. Light incoming from a fluorophore 80', is a vortex before and after the conical crystal 98.

The fluorophore 80" had been placed after the focal plane of the collimating lens, 82, at a distance of Δz on the lens system 98; it is placed at a distance of −2 Δz of the focal position, 99, and the light from the fluorophore 80" converge also to the output of the lens system, 98, after the front lens, 97. The light from the fluorophore 80", has already been converted into a vortex by one of conical diffraction setup consisting of collimating lens 81, and either one of the conical crystals 88 or 89, depending on the channel of polarization followed by the light. The conical crystal 101 changes the light from fluorophore 80", and, for relevant parameters of the material, i.e. the size and orientation of the conical crystal, it reverts to a regular wave, slightly different from the Airy disk.

The objective lens of the non-collimation path, 102, is adapted to focus the plane containing fluorophore 80", which is a regular wave, 104, and not the fluorophore 80', which is singular on the pixelated detector assembly, 103. The incident light emerging from a fluorophore positioned in plane 104, such as the fluorophore 80", is perfectly focused and is positioned at the center of the pixelated detector, 103. Incident light emerging from a fluorophore positioned at the plane 99 is a vortex and therefore focuses on an outer ring with a central zero. By separately recording the intensity at the center and the intensity at the outer part of the detector, it is possible to separate, with a slight overlap between the incident light planes 104 and 99. In addition, a fluorophore positioned at the plane 104 as the fluorophore 80, is slightly delocalized because the objective is calculated so as to focus on the detector plane 104. This improves the action of the optical module LongSRCS, pushing further the intensity of the vortex center and reducing duplication.

This simplified description of a preferred embodiment of the optical module LongSRCS, 800, allows many possibilities of variations and adaptations by changes in the optical design through changes known to one skilled in the art. These changes include, but are not limited to: the crystal material and orientations, the choice of polarization components, the choice of the polarization axes of the cascade elements, the number of sensors, or, reversing the roles of fluorophores 80' and 80". In addition, the module is ideally conditioned to be constructed as a set of monolithic subsets or even as a single monolithic unit.

Method PDOS and Lateral Measurements

Method PDOS was originally designed to allow longitudinal superresolution, however PDOS method can also be used for measuring the lateral position of a fluorophore. Indeed, the elementary light distributions are also sensitive to variation of the lateral position of the fluorophore. For a plane sample, in the case where the light projection is not possible, the method PDOS may replace the method PSIT for performing superresolution measurements All these variants of the measurement methodology are considered part of the invention. The inventor has yet chosen in the preferred implementation to separate into two disjoint, separated, but complementary optical modules the lateral measures from the longitudinal measures to reduce the complexity of each one of the add-ons.

Detection Module

The corollary of the potency of the measurement methodology is the requirement of a more complex detection module, able to detect and retrieve information created. In scanning confocal microscopy, the detector is a detector consisting of a single element as a PMT or SPAD. The acquisition time of the detector is determined by the scanning mechanism.

The measurement methodology requires, in some embodiments, two detector modules, instead of one, the fundamental and vortex detector modules. In addition, the measurement methodology requires, in some embodiments, for each illuminated volume, the acquisition of the optical information on a small spatial grid, typically 16*16, at a rate higher than the pixel time, due to the requirement to identify and quantify the sequential signals.

An improved detection module, 65, may be implemented using small detectors with low number of pixels. Such a module would not have been possible ten or twenty years ago, due to the lack of appropriate technologies. Today, small detectors with small number of pixels, at high speed, with low noise characteristics are available on the basis of several technologies: SPAD arrays with a small number of pixels, such as 32*32 have been shown recently with acquisition rates up to 1 MHz. The improved detector module 65, may also be implemented using CCD, EMCCD or CMOS sensors.

CCD sensors, CMOS and EMCCD with a small number of pixels exist or can be specifically designed. In addition, CCD sensors, CMOS EMCCD can be used using features as region of interest, sub-windowing or "binning", available in many detectors.

The spatio-temporal information referenced herein is the position and the time of the impact of each fluorescent photon. In real systems, the spatio-temporal information is corrupted by the noise of the detector, which creates incorrect photons, and by inefficient detection, creating photons which are not detected, thereby reducing performance. In SPAD arrays, for each photon, the pixel that has detected it and the time of impact are received, i.e. the full spatiotemporal information is available. For CCD sensors, CMOS or EMCCD, the acquisition of multiple frames is necessary to approximate the spatio-temporal information.

In several implementations we will refer to separate detectors; in many cases the sensor can be either physically separated or consisting of different areas on a single detector, or a combination of the two previous cases.

Algorithms SRCDA

As stated previously, the algorithmic SRCDA can be implemented using the inverse problem methods of estimating parameters methods known to those skilled in the art.

We also present an algorithm according to one embodiment, specific to the measurement methodology, based on a set of descriptors.

Referring now to FIG. 9, which is a simplified schematic illustration of a algorithmic method, 900, of superresolution of fluorophore's data in accordance with an embodiment of the present invention.

An algorithmic procedure, presented in the FIG. 9, quantifies the number of fluorophores, retrieves the attributes of each fluorophore and quantifies the accuracy of each output parameter.

The preprocessing procedure, 111, reorganized the spatiotemporal information, 110, in sets of superresolution images, 112. This can be done using a filter bank procedure. The data set is then a small series of small images, typically 16*16 pixels. The pretreatment procedure is applied to a small number, of the order of several thousand, of spatiotemporal elements; it can be performed in real time using existing hardware.

The procedure descriptor, 113, the main step of the calculation, created from each image, a set of descriptors, 114, and their statistical significance. Descriptors include, but are not limited to: the intensity of each image, the presence in the image of a light distribution and its characterization as a regular distribution or as a vortex, the center of gravity, and moments of first and higher orders.

The third step is a filtering operation, 115, wherein only the descriptors that are statistically relevant, are retained.

The classification operation, 116, is the last step of the algorithm. The algorithm is capable of recognizing, on the basis of the set of descriptors, 114, and a knowledge base, 117, where the measurement different cases as a single fluorophore, two fluorophores separated longitudinally or laterally and three or more fluorophores.

Note that, due to the amount of information created, numerous cases that were ambiguous in fluorescence microscopy will be clearly identified. For example, as described in more detail later, a single fluorophore must meet a long list of conditions and cannot be confused with a case of multi-fluorophore. Two longitudinally separated fluorophores will create independent sets of descriptors and two laterally separated fluorophores differ clearly on at least one descriptor from a single fluorophore.

Algorithm Process Consists Implementing Optical Measurement Methodology

The compound optical process according to at least one embodiment of the invention is the logical complement of the descriptors algorithm. Indeed, the result of the descriptors calculation procedure can lead to the conclusion that an additional image would improve performance of the measurement. The SRCDP microscopy platform allows the acquisition of one—or more additional images from a set of light distribution of the PSIT or PDOS methods.

An example is explained below.

Position Measuring Point by the Method PSIT

PSIT method can be used as a technique for measuring the position of a fluorophore with high precision. This measure can use the descriptors algorithm presented previously.

Consider a fluorophore positioned at the position x, y in Cartesian coordinates and $(\rho,\theta)$ in polar coordinates.

A sequence of illumination consisting of a fundamental wave, and a couple of the so-called "half-moon" distributions aligned along orthogonal axes is projected onto the fluorophore.

The preprocessing procedure created two images:
  A "top hat" image consisting of the sum of the three images of the sequence.
  A vortex image consisting of the sum of the two images half-moons.
  A first descriptor is the Cartesian position is calculated using the algorithm of the centroid of the image "top hat".

Referring to FIG. 10, the radial position p can be measured unambiguously by measuring a parameter, $\rho_a$, equal to the arctangent, of the intensity ratio between the normalized intensity emitted by illuminated by the fluorophore wave vortex, $I_v$, and the normalized intensity emitted by the fluorophore illuminated by the fundamental wave, $I_F$, normalized by a factor 7E. In fact:
  The normalized intensity emitted by the fluorophore illuminated by the fundamental wave varies from 1, at the center of the fundamental wave, to 0, at radius of Airy,
  the normalized intensity, emitted by the fluorophore illuminated by the vortex wave varies from 0 for the center of the vortex to 1 at the vortex maximum and reach 0 to a value slightly higher than the radius of Airy. The arc tangent of the ratio is a monotonic function.

The azimuth position can be measured by measuring the intensity ratio between the total intensity emitted by the fluorophore illuminated by the first half-moon distribution, $I_H$, and the total intensity emitted by the fluorophore illuminated by the second half moon distribution, $I_{ve}$. The ratio between these two intensities is a geometric tangent square law:

$$\frac{I_{VE}}{I_H} = \tan^2\theta \qquad (EQ.\ 9)$$

Both measures are redundant. This redundancy is a measure to qualify the observed object as a single point and separate it from other objects potentially present in the sample.

Representation in a Higher Dimensional Space: Cartesian-oPolar Representation

This result can be generalized. We introduce in this paper an entire new representation of a plane, combining the Cartesian representation and the polar representation. We named this representation the CartesianoPolar representation. A point in the plane is represented by a quadruplet: x, y, p, θ. This representation is non-Euclidean and redundant. A similar representation of space can be defined mutatis mutandis.

At first sight this representation seems unnecessary: it is a highly complex representation for a much simpler reality. It is well known that the position of a point in a plane can be represented, alternatively, either by using the Cartesian coordinates, x and y, or either by using polar coordinates p and θ.

Representation in a Higher Dimensional Space: Pythagoras Space

In this paper only the simplified version of the CartesianoPolar representation is detailed, wherein a point with coordinates x, y and p is represented. We named this space the space of Pythagoras.

Defining the geometric area to be a two-dimensional surface in three-dimensional space, which fills the constitutive geometric equation $\rho^2=x^2+y^2$; assumes a measurement system that simultaneously measures x, y and ρ, as the measurement system such as described in the previous paragraph together with a centroid algorithm on the same data. A point will be physically positioned in the space of Pythagoras, on the geometrical surface. Consider the case of two or more physical points: The center of gravity of the two points of measurement is outside the geometric surface and creates a point outside this area. This representation is a mathematical formalization and generalization of the deterministic algorithm for separating the case of an isolated point from that of an aggregate of points previously described.

Recognition and Measurement of Two Points: a New Resolution Criterion

Consider now two fluorophores positioned symmetrically about the center at positions, p, θ and p, −θ in polar coordinates. We will use the system described in the previous paragraphs. Three descriptors give the following results:

The centroid measure the centroid of the light distribution, which will be the origin, The identifier ρ, measure the value of the common radial value of the two fluorophores, The θ descriptor, which in the case of half-moons contains a degeneracy between θ and −θ, will measure the value θ.

As mentioned above, if the value of the descriptor ρ is not zero, we know that the case study is not a point but two or more. In addition, descriptors ρ and θ allow us to measure the characteristics of the two points at a much higher resolution than that defined by the Rayleigh criterion. Moreover, using a compound process it is possible to separate this case from the vast majority of cases of three or more points. An additional light distribution can be projected onto the sample, a half-moon inclined at an angle θ; the assumption of the presence of two points will be confirmed or refuted based on the results of this image. Indeed, the measured energy will be zero for two points, for a line or for a series of dots aligned in the direction of the angle θ.

Control Module

With reference to FIG. 11, the preferred embodiment of this invention, the invention further describes the various control elements integrated into the platform SRCDP, 500:

The control module, 1100, using the procedure of systemic control, 1101, monitors and modifies the optical parameters of the platform SRCDP, 500, the electronic parameters of the improved detection module, 65, and the mathematical parameters of algorithmic procedures SRCDA, 600, to optimize the emerging information in accordance with criteria defined by the system or by the user. Control is achieved by varying control systems 1102, 1103 and 1104, of the various elements of the platform, 600, 800 and 900. The control system 1100, also use, if available, external information, 1105, relayed by computer support.

Alternative Implementations of the Measurement Methodology

In one embodiment of the PSIT method, regular and singular waves are created by the propagation of a incident regular wave through a uniaxial crystal, replacing the conical crystal 32.

In another embodiment of the method PSIT, regular and singular waves are created by the positioning at the Fourier plane of an optical system of a phase plate—such as a spiral phase plate—or a subwavelength grating, or by positioning a suitable holographic optical element.

In another embodiment of the PSIT method—thick point, not shown, the illumination of the sample comprises a sequence of at least two compact compound light distributions, every compact compound light distribution being composed consisting itself of at least two simple compact light distributions projected simultaneously. Said at least two simple compact light distribution being optically coherent, partially coherent or incoherent relative to each other, said at least two simple compact light distributions being positioned at different spatial positions and said at least two simple compact light distributions differing in at least one of characteristics, such as their central lateral position, their central longitudinal position, their polarization, amplitude or phase. The ensemble of simple compact light distributions contains compact light distributions from different topological families.

In another embodiment of the PSIT method, not shown, compact light distributions are created by different modes of a multimode laser, and the sequence of compact light distributions is created by successively creating modes or, alternatively, by controlling the balance of energy between the modes.

In another embodiment of the PSIT method, not shown, the relationship between regular and singular wave is dynamically changed.

In another embodiment of the PSIT method, not shown, the regular wave and the singular wave are created by a physical separation of the incident beam—in at least—two paths, the transformation in one path, of the regular beam to singular being realized by known means such as phase plates or spiral phase plates, holographic optical element, subwavelength gratings, uniaxial or biaxial crystals or combination thereof, and the recombination of the two beams using a beam combiner into a single beam. In this embodiment, the differentiation of the compact light distributions can be performed either on the combined beam or on each beam, independently after separation and before recombination.

In another embodiment of the method PSIT, dynamic following, not shown, the system comprises means, including but not limited to controllable mirrors, electro-optical or acousto-optical devices or piezoelectric actuators capable to move the compact light distribution or the sequence of compact light distributions in space with high precision. In the system of dynamic monitoring, the position of the compact light distribution and of the sequence is dynamically controlled so as to follow at least one specific target.

In another embodiment of the method PSIT, black fluorophore, not shown, the compact light distribution or a mathematical combination of compact light distributions is configured so that there is zero intensity at the center of the compact light distribution. The system comprises means adapted to move through space the compact light distribution and these means are used to follow the fluorophore and for positioning the fluorophore at its center, a function of time. When the fluorophore is positioned at the center of the compact light distribution, without movement, its position can be measured with high accuracy without fluorescent light emerging from a fluorophore, thereby substantially reducing the effects of photo-bleaching. A movement of the fluorophore can be compensated by appropriate movement of the position of the compact light distribution to follow the fluorophore using a small amount of emitted fluorescent light.

In another embodiment of the method PSIT, dynamic sequences choice, not shown, the system dynamically determines, on the basis of a positioning hypothesis or of a first set of measures, the optimal sequence of compact light distributions.

In another embodiment of the method PSIT, sequences choice and dynamic positioning of the compact light distribution, not shown, the system comprises means, including but not limited to controllable mirrors, electro-optic and acousto-optic devices or piezoelectric actuators, capable of moving in space the compact light distribution, or a combination of compact light distributions with great precision. The system dynamically determines, on the basis of a positioning hypothesis or of a first set of measures, the optimal sequence and the position of the compact light distributions.

In another embodiment of the PSIT method, PSIT method of triangulation, two or more measurement process of the method PSIT, previously described, are carried out on the same sample with different projection axes. The variation in lateral position between the two measurements permits the measurement of the longitudinal position of nano emitter light.

In another embodiment of the PSIT method, the parallel PSIT method, light is incident on a micro lens array—or other optical means, known to those skilled in the art, allowing the realization of a set of light distributions in parallel, these light distributions being modified by an optical module to perform simultaneously the PSIT method on a large number of discrete points.

In another embodiment of the PSIT method the multispectral PSIT method (not shown), the sample is illuminated sequentially or simultaneously by at least two illumination sequences, each sequence projecting light onto the sample at different wavelengths In another embodiment of the method PDOS, not shown, the channeling of the incoming light from different point sources according to their longitudinal position is realized in the focal plane. It is carried out using an element having polarization properties dependent on the lateral position. Light entering from a point disposed longitudinally relative to a determined plane, will be incident on a given position and will have specific polarization properties, and the incident light from points located at different longitudinal—and lateral—positions, will be incident on other positions in the focal plane, which have different polarization characteristics.

As to a further discussion of the manner of usage and operation of the invention, it should be apparent from the above description. Therefore, any discussion on the form of the use and operation will not be described.

In this respect, before explaining at least one embodiment of the invention in detail, it is understood that the invention is not limited in its application to the details of construction and arrangements of the components set forth in the following description or illustrated in the drawing. The invention is capable of other embodiments and can be practiced and carried out in various ways. In addition, it is understood that the phraseology and terminology employed herein are for the purpose of description and should not be regarded as limiting.

References cited herein teach many principles that are applicable to the present invention. Therefore, the entire contents of these publications are incorporated herein by reference, as appropriate to the teachings of additional or alternative details, features and/or technical information.

The embodiments of the invention described can be integrated on a fluorescence confocal microscope. Superresolution system according to embodiments of the invention is a new method of measurement, in addition to or in replacement of existing methods of microscopy. However, the superresolution system according to embodiments of the invention may equally be integrated on other microscopy platforms. These microscopy platforms, as described as examples, include but are not limited to: wide field microscopes, Bright field microscope, dark field microscopes, polarization microscopes, phase difference microscopes, differential interference contrast microscopes, stereo microscopes, Raman microscopes, microscopes dedicated to a specific task, such as live cell imaging, cell sorting, cell motility or any other instrument optical microscopy as described for example in [4].

It is understood that the invention is not limited in its application to the details set forth in the description contained herein or illustrated in the drawings.

The invention is capable of other embodiments and of being practiced and carried out in various ways. Those skilled in the art will readily understand that various modifications and changes can be applied to the embodiments of the invention as described above without departing from its scope as defined in and by the appended claims.

What is claimed is:

1. A method of optical measurement for determining the spatial position of at least one luminous object in a sample, the method comprising:

projecting onto the sample a sequence of a first compact luminous distribution and a second compact luminous distribution, wherein the first and second compact luminous distributions are of different topological families;

detecting light re-emitted by said at least one luminous object of the sample;

generating from the detected light a first image of the at least one luminous object as illuminated by the first compact luminous distribution and a second image of the at least one luminous object as illuminated by the second compact luminous distribution; and algorithmically analyzing images to obtain spatial position information of the at least one luminous object.

2. A method according to claim 1 wherein the first and the second compact luminous distributions are collocated on the sample.

3. A method according to claim 1, wherein said first and second compact luminous distributions of different topological families are created by an interference between a regular wave and a singular wave, or between two singular waves, and a spatial differentiation between said at least two distributions is created by varying at least one of following parameters:

a) at least one of the parameters of the regular wave;

b) at least one parameter of at least one of the singular wave; and c) a phase difference between the regular wave and the singular wave or between two singular waves.

4. A method according to claim 3 further comprising at least one of the following steps:

controlling the relative amplitude of the regular or singular waves;

controlling in a predetermined sequence, the polarization or the phase state of the input light wave or output lightwave of a crystalline sub-module creating the regular and singular waves;
controlling the shape of the singular or regular waves; and
aligning the central position of a luminous distribution of one of the waves with respect to the other.

5. A method according to claim 1 further comprising:
separating an incident regular wave into two regular waves along geometric separate paths;
transforming at least one of the regular optical waves into a singular optical wave, and
merging the two emerging optical waves created.

6. A method according to claim 1 wherein said first and second compact luminous distributions are created by controlling the intensity of the different modes of a multimode laser.

7. A method according to claim 1 wherein a region of a size substantially less than an average wavelength of the re-emitted light is in the sample, wherein the value of a specific mathematical combination of at least one of intensities and amplitudes of said first and second compact luminous distributions of different topological families is positive for the positions of the portion of said compact luminous distributions included within said region, and wherein said specific mathematical combination is close to zero in all other parts of the first and second compact luminous distributions beyond said region.

8. A method according to claim 1 wherein at least one nanoemitter is a fluorophore with a sequence of luminous fluorescence intensities which depend on the incident intensity of a sequence of first and second compact luminous distributions of different topological families on said fluorophore thereby characterizing the spatial position of said fluorophore.

9. A method according to claim 1 wherein a region, having a size which is substantially less than the average wavelength of the re-emitted light, is present in the sample, wherein a comparison of a plurality of mathematical combinations of a sequence of said first and second compact luminous distributions of different topological families, is used to distinguish between at least one of the following:
a) a single luminous object;
b) a plurality of collocated luminous objects, and
c) a plurality of luminous objects located at a distance from each other, thereby determining the distance between the luminous objects.

10. A method according to claim 1 further comprising varying the sequence of said first and second compact luminous distributions, or the position of the sequence of said at least two luminous distributions as a function of at least one of measured data and external information.

11. A method according to claim 1 wherein the projection of luminous distributions of different topologies is performed by conical diffraction and modified by a variation of the polarization states at an input and output of at least one conical crystal performing the conical diffraction.

12. The method of optical measurement in accordance with claim 1, wherein the luminous object is a luminous nanoemitter.

13. The method of optical measurement in accordance with claim 1, further comprising:
retrieving at least one of a longitudinal position and a lateral position of a luminous object.

14. The method of optical measurement in accordance with claim 1, further comprising:
retrieving at least one of a longitudinal position and a lateral position of a luminous nano emitter.

15. The method of optical measurement in accordance with claim 1, further comprising:
projecting a plurality of elementary light distributions shifted longitudinally with respect to each other; and
algorithmically analyzing optical images to obtain a spatial position of said at least one luminous object in a longitudinal dimension.

16. The method of optical measurement in accordance with claim 1, further comprising:
projecting a plurality of elementary light distributions each characterized by a distinct longitudinal dependency; and
algorithmically analyzing optical images to obtain a spatial position of said at least one luminous object in a longitudinal dimension.

17. An optical measurement device for determining a spatial position of at least one luminous object of a sample, the apparatus comprising:
a. a projector for projecting onto the sample a sequence of a first compact luminous distribution and a second compact luminous distribution, the first and second compact luminous distributions being of different topological families;
b. a detector adapted to detect light re-emitted by said at least one luminous object of the sample;
c. an image generator adapted to generate from the detected light a first image for the first compact luminous distribution and a second image from the second compact luminous distribution; and
d. an analyzer for performing a computational analysis of images to obtain position information of said at least one luminous object.

18. The optical measurement device of claim 17, wherein the projector is configured to collocate the at least two compact luminous distributions on the sample.

19. The optical measurement device of claim 17, further comprising a light source, and comprising at least one of:
a. a crystalline sub-module, configured to create from an incident light wave, two collocated light waves, comprising one regular wave and one singular wave or two singular waves, the said crystalline submodule comprising a thin biaxial crystal or a uniaxial crystal;
b. an optical sub-module adapted to separate a regular incident wave into two regular waves along geometrically separated paths, said sub-module being configured to transform one of the regular optical waves into a singular wave, using an optical component comprising:
   i. a subwavelength grating; and
   ii. a thin biaxial or uniaxial crystal, wherein the optical sub-module is adapted to merge two emerging regular waves created;
c. a partial polarizer, adapted to control the relative amplitude of regular and singular waves and preferably to translate the central position of the luminous distribution of a wave with respect to the other;
d. an optical control sub-module for controlling the amplitude, polarization or phase, comprising at least one adjustable or controllable optical element for controlling, in a predetermined sequence, the amplitude, the polarization or phase state of the wave light input to or output from the crystalline sub-module;
e. a sub-control module comprising at least one adjustable optical element, for controlling the waveform of the regular or singular waves f. a polarization analyzer, and g. a submodule for shaping, statically or dynamically, a polarization of light emerging from the superposition of such light distributions in such a manner as to mitigate vector effects on the shape and size of each compact luminous distribution, and effects created by a large numerical aperture of the image generator by shaping the polarization emerging by providing a static polarization state that is rotationally symmetrical.

20. The optical measurement device of claim 19, wherein the projector is adapted to project a sequence of at least two compact luminous distributions of different topological families onto the sample in such a manner that a region of lateral size substantially less than an average wavelength of light emitted by the projector is located in the sample, and further comprising a comparator for comparing a plurality of mathematical combinations of said sequence of compact light distributions of different topological families for differentiating between at least two of the following:
   a. a single luminous nanoemitter or object;
   b. a plurality of collocated luminous objects; and
   c. a plurality of luminous objects located at a distance from each other, thereby determining the distance between the luminous objects.

21. The optical measurement device of claim 19, wherein the analyzer is configured to measure a position of said at least one luminous object.

22. The optical measurement device of claim 17, further comprising a multimode laser, wherein intensities of modes of the multimode laser are controllable in such a manner as to create at least two compact luminous distributions of different topological families.

23. The optical measurement device of claim 17, wherein the projector is adapted to project a sequence of said first and second compact luminous distributions of different topological families onto the sample in such a manner that a region of a lateral size substantially less than an average wavelength is re-emitted in the sample, wherein the value of a specific mathematical combination of the intensities or amplitudes of at least two families of compact luminous distributions created by the projector is positive for the lateral spatial positions included in said region, and wherein said specific mathematical combination is close to zero in all other parts of said first and second compact luminous distributions beyond said region.

24. The optical measurement device of claim 17, wherein at least one nanoemitter is a fluorophore with a sequence of fluorescent luminous intensities which depend on an incident intensity of a sequence of compact luminous distributions of different topological families on said fluorophore thereby characterizing the spatial position of said fluorophore.

25. The optical measurement device of claim 17, wherein the projector comprises:
   a. at least one conical crystal adapted to perform conical diffraction; and
   b. an adjuster for varying polarization states of an input and an output of said at least one conical crystal.

26. The optical measurement device of claim 17, wherein the projector is configured to vary a sequence of said at least two luminous distributions, and/or a position of the sequence of said at least two luminous distributions as a function of measured data or external information.

* * * * *